(12) United States Patent
Shimizu et al.

(10) Patent No.: US 9,029,513 B2
(45) Date of Patent: May 12, 2015

(54) ANTI-EGFR ANTIBODY AND USE THEREOF

(75) Inventors: Nobuyoshi Shimizu, Shinjuku-ku (JP); Atsushi Takayanagi, Shinjuku-ku (JP); Tetsuhiko Yoshida, Tsukuba (JP)

(73) Assignees: Toagosei Co. Ltd., Tokyo (JP); Keio University, Tokyo (JP)

( * ) Notice: Subject to any disclaimer, the term of this patent is extended or adjusted under 35 U.S.C. 154(b) by 55 days.

(21) Appl. No.: 13/701,947

(22) PCT Filed: Jun. 3, 2011

(86) PCT No.: PCT/JP2011/062810
§ 371 (c)(1),
(2), (4) Date: Dec. 21, 2012

(87) PCT Pub. No.: WO2011/152525
PCT Pub. Date: Dec. 8, 2011

(65) Prior Publication Data
US 2013/0142812 A1    Jun. 6, 2013

(30) Foreign Application Priority Data
Jun. 4, 2010    (JP) ................ 2010-128623

(51) Int. Cl.
C07K 16/30    (2006.01)
A61K 39/395   (2006.01)
C07K 16/28    (2006.01)

(52) U.S. Cl.
CPC ............ C07K 16/30 (2013.01); C07K 16/2863 (2013.01); A61K 39/39558 (2013.01); *C07K 2317/73* (2013.01)

(58) Field of Classification Search
None
See application file for complete search history.

(56) References Cited

U.S. PATENT DOCUMENTS

| 5,844,093 | A   |     | 12/1998 | Kettleborough et al. |
|-----------|-----|-----|---------|----------------------|
| 7,732,157 | B1  | *   | 6/2010  | Baron et al.         |
| 8,178,320 | B2  |     | 5/2012  | Shimizu et al.       |
| 2007/0009972 | A1 | * | 1/2007  | Chao et al.          |
| 2012/0270797 | A1 | * | 10/2012 | Wittrup et al.       |

FOREIGN PATENT DOCUMENTS

| JP | A-2006-025794 | 2/2006 |
| WO | WO 99/40214 A2 | 8/1999 |
| WO | WO 03/044198 A1 | 5/2003 |

OTHER PUBLICATIONS

Rudikoff et al., Single amino acid substitution altering antigen-binding specificity, Proc. Nat. Acad. Sci. USA, 79:1979-1983, 1982.*
Lamminnaki et al., Crystal structure of a recombinant anti-estradiol Fab fragment in complex with 17Beta-estradiol, J. Biol. Chem. 276(39):36687-36694, Sep. 28, 2001.*
MacCallum et al., Antibody-antigen interactions: contact analysis and binding site topography, J. Mol. Biol. 262:732-745, 1996.*

(Continued)

*Primary Examiner* — Claire Kaufman
(74) *Attorney, Agent, or Firm* — Oliff PLC

(57) ABSTRACT

A cell growth inhibitor that includes, as an antibody component, an artificially produced anti-EGFR antibody having specific binding capacity to EGFR which is characterized in that an epitope therefor is in a cysteine-rich subdomain 2 (C2 domain) and/or in a ligand-binding domain 1 (L1 domain) among four subdomains contained in the extracellular domain of EGFR.

9 Claims, 12 Drawing Sheets

(56) References Cited

OTHER PUBLICATIONS

Chen et al., Enhancement and destruction of antibody function by somatic mutation: Unequal occurrence is controlled by V gene combinatorial associations, EMBO J., 14 (12): 2784-2794, 1995.*

Ozawa et al., "Selective Killing of Squamous Carcinoma Cells by an Immunotoxin that Recognizes the EGF Receptor", *International Journal of Cancer*, 1989, vol. 43, pp. 152-157.

Hirota et al., "Suppression of an Epidermal Growth Factor Receptor-hyperproducing Tumor by an Immunotoxin Conjugate of Gelonin and a Monoclonal Anti-Epidermal Growth Factor Receptor Antibody", *Cancer Research*, Dec. 15, 1989, vol. 49, pp. 7106-7109.

Osaku et al., "Targeted Killing of Squamous Carcinoma Cells by a Monoclonal Antibody-Peplomycin Conjugate which Recognizes the EGF Receptor", *Anticancer Research*, 1991, vol. 11, pp. 1951-1956.

Behzadian et al., "Monoclonal Antibody that Immunoreacts with a Subclass of Human Receptors for Epidermal Growth Factor", *Cell Structure and Function*, 1985, vol. 10, pp. 219-232.

Suzuki et al., "Targeted gene delivery using humanized single-chain antibody with negatively charged oligopeptide tail", *Cancer Science*, May 2004, vol. 95, No. 5, pp. 424-429.

Chang et al., "Screening of scFv-displaying phages recognizing distinct extracellular domains of EGF receptor by target-guided proximity labeling method", *Journal of Immunological Methods*, 2011, vol. 372, pp. 127-136.

Extended European Search Report issued in European Application No. 11789926.0 issued Dec. 11, 2013.

Takayanagi et al., "Cancer therapy with monoclonal antibody against EGFR," *Surgery Frontier*, 2002, pp. 226-230, vol. 9, No. 3, Japan (with English abstract).

Smith et al., "A Wortmannin-Cetuximab as a Double Drug", *Bioconjugate Chem.*, 2009, pp. 2185-2189, vol. 20, No. 11, American Chemical Society, USA.

Chang et al., "Characterization of Anti-EGF receptor ScFv Antibodies Selected from Phage Display Library," *Biochemistry*, 2008, pp. IP-1337, vol. 1 (with translation).

Takayanagi et al., "(O-432) Screening of recombinant antibodies against different epitopes using the existing monoclonal antibody as a guide molecule," *Annual Meeting of the Japanese Cancer Association*, Aug. 28, 2006, pp. 259, vol. 65, Japan (with translation).

Ito et al., "(P29[S]pm-557) Effect of anti-EGF receptor antibodies on signaling and proliferation of human non-small-cell lung cancer strains," *Annual Meeting of Pharmaceutical Society of Japan*, Mar. 6, 2006, pp. 100, vol. 126, No. 2, Japan (with translation).

Gamou et al., "Expression of EGF receptor subfamily in tumor," *Nihon Rinsho*, Jun. 1996, pp. 1521-1528, vol. 54, No. 6 (with English abstract).

International Preliminary Report on Patentability issued in International Application No. PCT/JP2011/062810 dated Jan. 8, 2013.

International Search Report issued in International Application No. PCT/JP2011/062810 dated Aug. 30, 2011.

* cited by examiner

ANTI-EGFR ANTIBODY AND USE THEREOF

TECHNICAL FIELD

The present invention relates to an artificially designed antibody and use thereof. More specifically, the present invention relates to an artificial antibody which specifically binds to epidermal growth factor receptor of human cells and use thereof.

The present application claims the priority based on Japanese Patent Application No. 2010-128623 filed on Jun. 4, 2010, the entire content of which is incorporated herein by reference.

BACKGROUND ART

It is known that cell growth or proliferation is promoted by binding of the epidermal growth factor (hereinafter referred to as "EGF") as a ligand to an extracellular domain of a receptor on the cell surface, i.e., epidermal growth factor receptor (hereinafter referred to as "EGFR"). Particularly, it has been found that EGFRs are overexpressed on the surface of various tumor cells and are deeply involved in growth and malignant conversion of the tumors.

Therefore, development of drugs which can block the binding of EGF to EGFRs to block signal transduction to which EGFRs are involved, resulting in suppression of growth of malignant tumor cells, particularly antibody drugs (anti-tumor drugs) mainly including antibodies which specifically bind to EGFRs (anti-EGFR antibodies) have been in progress. For example, anti-EGFR antibodies, matuzumab and cetuximab, have been known which can bind to EGFRs competitively with EGF, thereby inhibiting activation and dimerization of EGFRs, and their certain benefits have been shown in growth suppression (growth inhibition) of malignant tumor cells such as colon cancer cells. Patent Literature 1 discloses an example of conventional antibodies of this type and a production example thereof.

CITATION LIST

Patent Literature

Patent Literature 1: Japanese Patent Application Publication No. 2006-25794
Patent Literature 2: PCT International Publication No. WO 2003/044198

SUMMARY OF INVENTION

However, it has been reported that the conventional anti-EGFR antibodies such as those described above (e.g., cetuximab described above) have extremely low effect (cell growth suppression effect) and substantially not efficacious against KRAS mutant malignant tumor cells (cancer cells) such as certain types of colon cancer cells. Accordingly, there is a need for development of antibody drugs which have high cell growth suppression effect even against these KRAS mutant malignant tumor cells.

Thus, the present invention has been caused so as to solve the above conventional problem and one objective is to provide a new cell growth suppressing agent (cell growth inhibitor) which shows preferable cell growth suppression effect even against KRAS mutant cells which express EGFRs at a high rate and for which conventional antibody drugs, for example, have not been highly effective. Another objective of the present invention is to create a new anti-EGFR antibody which is used as a component of the cell growth inhibitor. Another objective of the present invention is to provide a method for suppressing (inhibiting) growth of target EGFR-expressing cells (particularly KRAS mutant malignant tumor cells) by using the anti-EGFR antibody disclosed herein.

The extracellular domain (typically consists of 621 amino acid residues) of human epidermal growth factor receptor (EGFR) contains four subdomains, which are, following a secretory signal sequence consisting of 24 amino acid residues, from the N-terminal of the amino acid sequence:

(1) "ligand-binding subdomain 1 (hereinafter referred to as "L1 domain"; a domain typically consisting of 165 amino acid residues at positions 25 to 189 from the N-terminal following the signal sequence)";

(2) "cysteine-rich subdomain 1 (hereinafter referred to as "C1 domain"; a domain typically consisting of 144 amino acid residues at positions 190 to 333 following the above L1 domain)";

(3) "ligand-binding subdomain 2 (hereinafter referred to as "L2 domain"; a domain typically consisting of 172 amino acid residues at positions 334 to 505 following the above C1 domain)"; and (4) "cysteine-rich subdomain 2 (hereinafter referred to as "C2 domain"; a domain typically consisting of 140 amino acid residues at positions 506 to 645 following the above L2 domain)", in this order. The conventional anti-EGFR antibodies such as those disclosed in the above Patent Literature 1 have the nature of mainly binding to the above (3) L2 domain.

The present inventors have artificially prepared anti-EGFR antibodies which are derived from the phage library in their possession and recognize epitopes different from those of conventional antibodies, and found that growth of so-called KRAS mutant cells (e.g., colon cancer cells), whose growth has not been shown to be effectively suppressed with conventional antibody drugs, can be suitably suppressed by using the obtained respective anti-EGFR antibodies or the combinations thereof, thereby completing the present invention.

Thus, one of the antibodies disclosed herein is an anti-EGFR antibody having specific binding capacity to epidermal growth factor receptor (EGFR) and produced artificially, characterized in that:

an epitope therefor is in a cysteine-rich subdomain 2 (C2) which is the fourth subdomain from the N-terminal of the extracellular domain of EGFR among four subdomains contained therein, a heavy chain variable region (VH region) thereof has an amino acid sequence of SEQ ID NO: 1 or a modified amino acid sequence obtained by substitution, deletion and/or addition of one to several amino acid residues with respect to the amino acid sequence of SEQ ID NO: 1 and retaining the specific binding capacity, and a light chain variable region (VL region) thereof has an amino acid sequence of SEQ ID NO: 2 or a modified amino acid sequence obtained by substitution, deletion and/or addition of one to several amino acid residues with respect to the amino acid sequence of SEQ ID NO: 2 and retaining the specific binding capacity.

The above anti-EGFR antibody is referred to as "C2 domain-binding anti-EGFR antibody" hereinbelow.

Another antibody disclosed herein is an anti-EGFR antibody having specific binding capacity to epidermal growth factor receptor (EGFR) and produced artificially, characterized in that:

an epitope therefor is in a ligand-binding domain 1 (L1) which is the first domain from the N-terminal of the extracellular domain of EGFR among four subdomains contained therein, a heavy chain variable region (VH region) thereof has an amino acid sequence of SEQ ID NO: 3 or a modified amino acid sequence obtained by substitution, deletion and/or addition of one to several amino acid residues with respect to the amino acid sequence of SEQ ID NO: 3 and retaining the specific binding capacity, and a light chain variable region (VL region) thereof has an amino acid sequence of SEQ ID NO: 4 or a modified amino acid sequence obtained by substitution, deletion and/or addition of one to several amino acid residues with respect to the amino acid sequence of SEQ ID NO: 4 and retaining the specific binding capacity.

The above anti-EGFR antibody is referred to as "L1 domain-binding anti-EGFR antibody" hereinbelow.

The term "epitope" as used herein refers to a binding portion in EGFR which is recognized by the subject anti-EGFR antibody and which has high affinity (binding activity). Therefore, the expression "an epitope therefor is in a L1 domain (or C2 domain)" for example, means that the subject anti-EGFR antibody selectively binds to the L1 domain (or C2 domain) with high affinity (specificity) by antigen-antibody reaction compared to other subdomains in the extracellular domain.

The C2 domain-binding anti-EGFR antibody and L1 domain-binding anti-EGFR antibody generated by the present inventors can suitably suppress growth of high EGFR expressing cells including KRAS mutant cells (e.g., malignant tumor cells such as colon cancer cells). Accordingly, the above artificial antibodies disclosed herein can provide antibody drugs which has high efficacy in growth suppression of high EGFR expressing cells (e.g., KRAS mutant cancer cells).

A preferable aspect of the antibodies disclosed herein is characterized in that the antibodies are in the form of human IgG containing a heavy chain constant region (CH region) and a light chain constant region (CL region) of human IgG in addition to the VH region and the VL region. The configuration in the form of human IgG makes the antibodies more suitable for use in patients.

The present invention also provides a cell growth inhibitor which is prepared with the anti-EGFR antibodies disclosed herein.

Namely, the cell growth inhibitor disclosed herein is a cell growth suppressing agent (cell growth inhibitor) for suppressing growth of at least one epidermal growth factor receptor (EGFR)-expressing cell, comprising either or both of the antibodies which have features as described in the following (A) and (B):

(A) C2 Domain-Binding Anti-EGFR Antibody:

an artificially produced anti-EGFR antibody having specific binding capacity to EGFR, wherein:

an epitope therefor is in a cysteine-rich subdomain 2 (C2) which is the fourth subdomain from the N-terminal of the extracellular domain of EGFR among four subdomains contained therein, a heavy chain variable region (VH region) thereof has an amino acid sequence of SEQ ID NO: 1 or a modified amino acid sequence obtained by substitution, deletion and/or addition of one to several amino acid residues with respect to the amino acid sequence of SEQ ID NO: 1 and retaining the specific binding capacity, and a light chain variable region (VL region) thereof has an amino acid sequence of SEQ ID NO: 2 or a modified amino acid sequence obtained by substitution, deletion and/or addition of one to several amino acid residues with respect to the amino acid sequence of SEQ ID NO: 2 and retaining the specific binding capacity; and (B) L1 Domain-Binding Anti-EGFR Antibody:

an artificially produced anti-EGFR antibody having specific binding capacity to EGFR, wherein:

an epitope therefor is in a ligand-binding domain 1 (L1) which is the first domain from the N-terminal of the extracellular domain of EGFR among four subdomains contained therein, a heavy chain variable region (VH region) thereof has an amino acid sequence of SEQ ID NO: 3 or a modified amino acid sequence obtained by substitution, deletion and/or addition of one to several amino acid residues with respect to the amino acid sequence of SEQ ID NO: 3 and retaining the specific binding capacity, and a light chain variable region (VL region) thereof has an amino acid sequence of SEQ ID NO: 4 or a modified amino acid sequence obtained by substitution, deletion and/or addition of one to several amino acid residues with respect to the amino acid sequence of SEQ ID NO: 4 and retaining the specific binding capacity.

The cell growth inhibitor typically comprises at least one pharmaceutically acceptable carrier.

Preferably, the antibody comprised in the cell growth inhibitor is in the form of human IgG containing, in addition to the VH region and the VL region, a heavy chain constant region (CH region) and a light chain constant region (CL region) of human IgG.

The cell growth inhibitor disclosed herein can suppress (inhibit) growth of not only general high EGFR expressing cells but also KRAS mutant cells because the antibody component thereof is the C2 domain-binding anti-EGFR antibody and/or L1 domain-binding anti-EGFR antibody whose epitope is different from those for conventional anti-EGFR antibodies.

Thus, according to the present invention, the cell growth inhibitor which targets a KRAS mutant malignant tumor cell as the EGFR-expressing cell and which suppresses growth of the KRAS mutant malignant tumor cell can be provided.

The present invention also provides a method for suppression of growth of at least one epidermal growth factor receptor (EGFR)-expressing cell, characterized in that it uses the C2 domain-binding anti-EGFR antibody and/or L1 domain-binding anti-EGFR antibody disclosed herein (preferably the one in the form of human IgG) and that it comprises applying the anti-EGFR antibody(s) to the target EGFR-expressing cell.

One suitable aspect of the method for suppression of cell growth may include a method in which the EGFR-expressing cell is a KRAS mutant malignant tumor cell and the method is used for suppressing growth of the KRAS mutant malignant tumor cell.

The present invention also provides various polynucleotides designed artificially (e.g., a plasmid used as an expression vector as described hereinbelow) which is used for production of the anti-EGFR antibodies disclosed herein by genetic engineering techniques. Typically, the present invention provides an polynucleotide designed artificially which comprises a nucleotide sequence encoding at least one amino acid sequence from SEQ ID NOs: 1 to 4 disclosed herein and which is for expressing a peptide comprising an amino acid sequence encoded by the nucleotide sequence (i.e., the amino acid sequence constituting any of VH and VL regions disclosed herein).

DESCRIPTION OF EMBODIMENTS

Figure 1A:
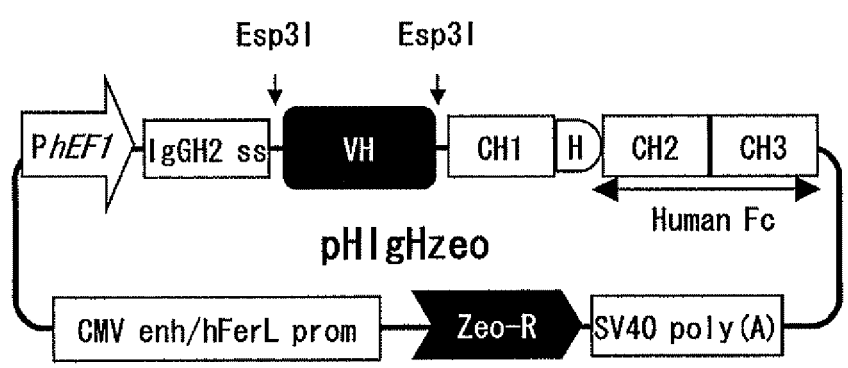
FIG. 1A is a plasmid map depicting an overview of an expression plasmid vector "pHIgHzeo"

Preferable embodiments of the present invention are described hereinbelow. The matters which are not specifically referred to in the present specification and which are necessary for practice of the present invention (e.g., gene recombinant techniques, protein (antibody) purification and general matters relating to bioassays) may be understood as matters which a person skilled in the art can appropriately design based on conventional techniques in the fields of cell engineering, medical science, pharmaceuticals, organic chemistry, biochemistry, genetic engineering, protein engineering, molecular biology and the like.

The present invention can be practiced based on the contents disclosed herein and common technical knowledge in the art.

All literatures cited herein are incorporated herein by reference in their entirety.

The term "antibody produced artificially" as used in the present specification means an antibody which is artificially produced typically by genetic engineering techniques and is different from an antibody produced by natural immunoreactions in human or animal in vivo.

The term "antibody" typically denotes an immunoglobulin containing a heavy chain and a light chain and encompasses immunoglobulin molecules in native form (typically IgG, e.g., human IgG) as well as various fragment antibodies such as Fab fragments and F(ab')$_2$ fragments.

The "antibody" as used in the present specification encompasses an antibody molecule which may be formed by genetic engineering techniques. For example, so-called single-chain antibodies (scFvs) produced artificially which comprise an amino acid sequence of a VL region and an amino acid sequence of a VH region on a single peptide chain are also encompassed by the "antibody" used in the present specification.

The term "amino acid residue" as used in the present specification encompasses an N-terminal amino acid and a C-terminal amino acid of a peptide chain unless otherwise stated.

The term "modified amino acid sequence" as used in the present specification in the context of given amino acid sequences forming the VH or VL region means an amino acid sequence which is formed by substitution, deletion and/or addition (insertion) of one to several (e.g., one, two or three) amino acid residues without deteriorating the antigen binding capacity of the given amino acid sequences. For example, sequences resulting from so-called conservative amino acid replacement in which one to several (typically two or three) amino acid residues are conservatively substituted (e.g., sequences in which a basic amino acid residue is substituted by another basic amino acid residue and sequences in which an acidic amino acid residue is replaced by another acidic amino acid residue) or sequences obtained by adding (inserting) or deleting one to several (typically two or three) amino acid residues to or from the given amino acid sequences are typical examples encompassed by the modified amino acid sequence according to the present specification.

The term "polynucleotide" as used herein refers to a polymer (nucleic acids) of more than one nucleotides linked by phosphodiester bonds and is not limited by the number of nucleotides. The polynucleotide as used herein encompasses DNA fragments having various lengths.

The term "polynucleotide designed artificially" means a polynucleotide whose nucleotide chain alone (full length) does not occur naturally and which is artificially synthesized by chemical synthesis or biosynthesis (i.e., genetic engineering production). For example, recombinant plasmid DNAs, recombinant phage DNAs and the like comprising a nucleotide sequence encoding the amino acid sequence disclosed herein are typical examples encompassed by the artificially designed polynucleotide according to the present specification.

The cell growth inhibitor provided by the present invention is a composition which comprises at least one antibody created by the present inventors (i.e., the C2 domain-binding anti-EGFR antibody and/or L1 domain-binding anti-EGFR antibody) and is characterized in that it suppresses growth of at least one EGFR-expressing cell. Other components contained and preparation, storage, usage and the like as a drug may be the same as those for conventional antibody drugs (pharmaceutical compositions containing antibodies) without particular limitation. For example, pharmaceutically acceptable carriers may include saline, PBS and other buffers, Ringer's solution and the like. Additives may include various antibiotics, pH adjusting agents, antioxidants, chelating agents, pigments, preservatives, various vitamins, enzymes and the like.

The present inventors screened the phage display single-chain antibody library which was constructed and possessed by the present inventors and colleagues (Patent Literature 2, supra, may be referred to as an example for the production of this kind of library) using a known anti-human EGFR monoclonal antibody as a so-called guide molecule, selected some new single-chain antibodies (scFvs) having an epitope different from those of conventional anti-EGFR antibodies and identified amino acid sequences corresponding to the variable regions of these scFvs and nucleotide sequences encoding the amino acid sequences to complete the present invention.

Namely, one suitable anti-EGFR antibody disclosed herein (C2 domain-binding anti-EGFR antibody) is an antibody characterized in that the VH region thereof has an amino acid sequence of SEQ ID NO: 1 (or a modified amino acid sequence thereof) and/or the VL region thereof has an amino acid sequence of SEQ ID NO: 2 (or a modified amino acid sequence thereof), and is a novel, artificially produced antibody whose epitope is in the C2 domain.

Another suitable anti-EGFR antibody disclosed herein (L1 domain-binding anti-EGFR antibody) is an antibody characterized in that the VH region thereof has an amino acid sequence of SEQ ID NO: 3 (or a modified amino acid sequence thereof) and/or the VL region thereof has an amino acid sequence of SEQ ID NO: 4 (or a modified amino acid sequence thereof), and is a novel, artificially produced antibody whose epitope is in the L1 domain.

The antibodies disclosed herein can be easily produced by genetic engineering techniques because the amino acid sequences of the variable regions which bind to the epitopes are apparent.

For example, single chain antibodies (scFvs) obtained from the above library may be sufficiently used as the antibody drug; however, in order to improve binding affinity in vivo and impart physical stability, it is preferable that they are in a complete antibody form (e.g., human IgG). As shown in Examples hereinbelow, they can be easily produced by amplifying by conventional PCR (Polymerase Chain Reaction) technique a nucleotide sequence encoding the VH region (VH gene) and a nucleotide sequence encoding the VL region (VL gene) from a plasmid vector comprising a nucleotide sequence encoding the scFv, introducing them in an antibody expression vector (such as a plasmid) having constant regions (CH and CL regions) and expressing in certain host cells (typically animal cells such as CHO (Chinese Hamster Ovary) cells).

Thus, the present invention provides a method for production of the anti-EGFR antibodies characterized in that it utilizes nucleotide information (i.e., nucleotide sequences) encoding the amino acid sequences of the VH and/or VL region(s) disclosed herein.

The cell growth inhibitor disclosed herein contains at least one of the C2 domain-binding anti-EGFR antibody and/or L1 domain-binding anti-EGFR antibody created by the present inventors as an antibody component, and as a result, as apparent from Examples described hereinbelow, can effectively suppress growth of KRAS mutant, high EGFR expressing cells (e.g., metastatic colon cancer cells), for which conventional antibodies of similar type have not been efficacious, as well as of high EGFR expressing cells without KRAS mutation.

Thus, the present invention can provide a method for controlling malignant tumor containing KRAS mutant, high EGFR expressing cells such as metastatic colon cancer, characterized in that it comprises administering to a patient at least one of the C2 domain-binding anti-EGFR antibody and/or L1 domain-binding anti-EGFR antibody disclosed herein (i.e., a drug composition containing the antibody(s)).

Dosages, dosage frequencies and dosage modes (oral, subcutaneous injection, intravenous injection, enema, etc.) may be varied according to the conditions (symptoms) of target patients, morphology of the administration target (malignant tumor), the form of the cell growth inhibitor used (drug composition), the form of the antibody(s) (e.g., whether it is in the form of scFv or complete human IgG), the concentration of the contained antibody(s), the presence or absence of auxiliary component(s) other than the antibody(s) and the concentration thereof and the like, and thus are design choices. A person skilled in the art can, as appropriate, based on the knowledge in known antibody engineering techniques as well as the knowledge in pharmaceuticals, clinical medicine, physiology or hygiene, prepare the cell growth inhibitor in a suitable form and administer (apply) the cell growth inhibitor (antibody drug) in the suitable form to the body of a given patient or cultures of tissue and cells from the patient. As the present invention is not characterized by this point per se, further detailed description is omitted.

The present invention is further described in detail based on the following Examples. However, the present invention is not intended to be limited by the following Examples.

TEST EXAMPLE 1

Production of Anti-EGFR Antibodies

The phage display single-chain antibody (scFv) library which was prepared beforehand was screened by using a mouse-derived anti-human EGFR monoclonal antibody which was created by the present inventors and colleagues and is commercially available as "B4G7" monoclonal antibody as a guide molecule. ScFv displaying phages which bound in the vicinity of the guide molecule were selectively collected and in the end four novel anti-EGFR single-chain antibodies (scFVs) in total and genes encoding the antibodies were obtained.

The obtained scFv genes were amplified by PCR using predetermined primers to identify the nucleotide sequences of the VH region and the amino acid sequences encoded thereby and the nucleotide sequences of the VL region and the amino acid sequences encoded thereby.

Amino acid sequence and nucleotide sequence information on the obtained four antibody samples (designated as sample Nos. 45, 38, 40 and 42) is as follows.

TABLE 1

Amino acid sequence and nucleotide sequence of sample No. 45

<VH region: SEQ ID NO: 1>
GlnValGlnLeuGlnGluTrpGlyAlaGlyLeuLeuLysProSerGluThrLeuSerLeuThrC
ysAlaValTyrGlyGlySerPheSerAspTyrTyrTrpSerTrpIleArgGlnProProGlyLy
sGlyLeuGluTrpIleGlyGluIleSerHisSerGlySerThrGlyTyrAsnProSerLeuLys
SerArgValAlaIleSerValAspThrProLysAsnGlnPheSerLeuLysLeuAsnSerValT
hrAlaAlaAspThrAlaLeuTyrTyrCysAlaArgLeuThrThrValValGlyGlyAsnTrpPh
eAspProTrpGlyGlnGlyThrLeuValThrValSerSerAla <VH region: SEQ ID NO: 9>
CAGGTGCAGCTGCAGGAGTGGGGCGCAGGACTGTTGAAGCCTTCGGAGACCCTGTCCCTCACCT
GCGCTGTGTACGGTGGGTCCTTCAGTGATTACTACTGGAGCTGGATCCGGCAGCCCCCAGGGAA
GGGGCTGGAGTGGATCGGAGAAATCAGTCATAGCGGAAGTACCGGCTACAACCCGTCCCTCAAG
AGTCGAGTCGCCATATCAGTTGACACGCCCAAGAACCAGTTCTCCCTGAAGCTGAACTCTGTGA
CCGCCGCGGACACGGCTCTATATTATTGTGCGAGACTGACAACAGTGGTTGGGGGCAACTGGTT
CGACCCCTGGGGCCAGGGAACCCTGGTCACCGTCTCCTCAGCG TABLE 1-continued Amino acid sequence and nucleotide sequence of sample No. 45

<VL region: SEQ ID NO: 2>
GlnSerValLeuThrGlnProProSerAlaSerGlyThrProGlyGlnGlyValThrIleSerC
ysSerGlySerSerAlaAspIleGlyAlaAsnTyrValTyrTrpTyrGlnGlnLeuProGlyTh
rAlaProLysLeuLeuIleTyrSerIleAsnGlnArgProSerGlyValProAspArgPheSer
GlySerLysSerGlyThrSerAlaSerLeuAlaIleSerGlyLeuArgSerGluAspGluAlaA
spTyrTyrCysAlaThrTrpAspAspSerLeuGlyGlyTrpAlaPheGlyGlyGlyThrLysVa
lGluIleLysArgThrValAla <VL region: SEQ ID NO: 10>
CAGTCTGTTCTGACTCAGCCCCCTTCCGCGTCTGGGACCCCCGGGCAGGGGGTCACCATCTCTT
GTTCTGGAAGGAGTGCCGACATCGGAGCAAATTATGTATACTGGTACCAGCAACTTCCAGGAAC
GGCCCCCAAACTCCTCATCTATTCTATTAATCAGCGGCCCTCAGGGGTCCCTGACCGATTCTCT
GGCTCCAAGTCTGGCACCTCAGCCTCCCTGGCCaTCAGTGGGCTCCGGTCCGAGGATGAGGCTG
ATTATTACTGTGCAACATGGGATGACAGCCTGGGTGGCTGGGCATTCGGCGGAGGGACCAAGGT
GGAAATCAAACGAACTGTGGCG

TABLE 2

Amino acid sequence and nucleotide sequence of sample No. 38

<VH region: SEQ ID NO: 3>
GlnValGlnLeuGlnGluSerGlyProGlyLeuValLysProSerGluThrValSerLeuThrC
ysSerValSerGlyAspSerLeuSerHisAsnTyrTrpSerTrpIleArgGlnProProGlyLy
sGlyLeuGluTrpIleGlyTyrIleTyrProSerGlyThrSerGlyThrThrLysTyrAsnPro
SerLeuLysSerArgValThrIleSerSerAspThrSerLysAsnGlnPheSerLeuArgLeuT
hrSerValThrAlaAlaAspThrAlaIleTyrTyrCysAlaLysGluAlaIleThrAlaAsnAl
aTrpProValSerAspTyrTrpGlyGlnGlyThrLeuValThrValSerSerAla <VH region: SEQ ID NO: 11>
CAGGTGCAGCTACAGGAGTCGGGCCCAGGACTGGTGAAGCCTTCGGAGACCGTGTCCCTCACCT
GCAGTGTCTCTGGTGACTCCCTCAGTCATAACTACTGGAGTTGGATCCGGCAGCCACCAGGGAA
GGGACTGGAGTGGATTGGGTATATCTATCCTAGTGGGACTAGTGGGACCACCAAGTACAATCCC
TCCCTCAAGAGTCGAGTCACCATATCAAGCGACACGTCCAAGAACCAGTTCTCCCTGAGGTTGA
CCTCTGTGACCGCTGCGGACACGGCCATATATTATTGTGCGAAAGAGGCAATCACCGCCAATGC
CTGGCCGGTGTCGGACTACTGGGGCCAGGGAACCCTGGTCACCGTCTCCTCAGCG <VL region: SEQ ID NO: 4>
AspIleValLeuThrGlnSerProAlaThrLeuSerLeuSerProGlyGluArgAlaThrLeuS
erCysArgAlaSerGlnSerValSerSerTyrLeuAlaTrpPheGlnGlnLysProGlyGlnAl
aProArgLeuLeuIleTyrAspAlaSerAsnArgAlaThrGlyValProAlaArgPheSerGly
SerGlySerGlyThrAspPheThrLeuThrIleThrSerLeuGluProGluAspPheAlaValT
yrTyrCysGlnGlnArgGlyAspTrpProLeuThrPheGlyGlyGlyThrLysValGluIleLy
sArgThrValAla <VL region: SEQ ID NO: 12>
GATATTGTATTGACCCAGTCTCCAGCCACCCTGTCTTTGTCTCCAGGGGAAAGAGCCACCCTCT
CCTGCAGGGCCAGTCAGAGTGTTAGCAGCTACTTAGCCTGGTTCAACAGAAACCTGGCCAGGC
TCCCAGGCTCCTCATCTATGATGCATCCAACAGGGCCACTGGCGTCCCAGCCAGGTTCAGTGGC
AGTGGGTCTGGGACAGACTTCACTCTCACCATCACCAGCCTAGAGCCTGAAGATTTTGCAGTTT
ATTACTGTCAGCAGCGTGGCGACTGGCCGCTCACTTTCGGCGGAGGGACCAAGGTGGAAATCAA
ACGAACTGTGGCG

TABLE 3

Amino acid sequence and nucleotide sequence of sample No. 40

<VH region: SEQ ID NO: 5>
GlnValGlnLeuValGlnSerGlyProGlyLeuValLysProSerGluThrLeuSerLeuThrC
ysThrValSerGlyGlySerValSerSerGlyThrTyrCysTrpSerTrpIleArgGlnProPr
oGlyLysGlyLeuGluTrpIleAlaTyrIleCysAsnSerGlySerThrSerTyrAsnProSer
LeuLysSerArgGlyThrIleSerValAspThrSerLysAsnGlnPheSerLeuArgLeuSerS
erValThrAlaAlaAspThrAlaValTyrTyrCysAlaArgLeuSerLeuIleMetValTyrHi
sIlePheAspTyrTrpGlyGlnGlyThrLeuValThrValSerSerAla <VH region: SEQ ID NO: 13>
CAGGTGCAGCTGGTGCAATCTGGCCCAGGACTGGTGAAGCCTTCGGAGACCCTGTCCCTCACCT
GCACTGTCTCTGGTGGCTCCGTCAGCAGTGGTACTTACTGCTGGAGCTGGATCCGGCAGCCCCC
AGGGAAGGGACTGGAGTGGATTGCGTATATCTGTAACAGTGGGAGCACCAGCTACAACCCCTCC TABLE 3-continued Amino acid sequence and nucleotide sequence of sample No. 40

CTCAAGAGTCGAGGCACCATATCAGTAGACACGTCCAAGAACCAGTTCTCCCTAAGGCTGAGCT
CTGTGACCGCTGCGGACACGGCCGTATATTACTGTGCGAGATTGTCGCTAATAATGGTGTATCA
TATCTTTGACTACTGGGGGCAGGGAACCCTGGTCACCGTCTCCTCAGCG

<VL region: SEQ ID NO: 6>
AspIleValMetThrGlnThrProAspSerLeuAlaValSerLeuGlyGluArgAlaThrIleA
snCysLysSerSerGlnAsnLeuLeuTyrThrSerSerAsnGlnThrTyrLeuAlaTrpTyrGl
nGlnLysProGlyGlnProProLysLeuLeuIleTyrTrpAlaSerThrArgGluSerGlyVal
ProAspArgPheSerGlySerGlySerGlyThrAspPheThrLeuThrLeuSerSerLeuGlnP
roGluAspValAlaAlaTyrTyrCysGlnGlnTyrTyrArgThrProIleThrPheGlyProGl
yThrLysValGluIleLysArgThrValAla <VL, region: SEQ ID NO: 14>
GATATTGTGATGACGCAGACTCCAGACTCCCTGGCTGTGTCTCTGGGCGAGAGGGCCACCATCA
ACTGCAAGTCCAGTCAGAATCTCTTATACACTTCCAGTAATCAGACCTACTTAGCTTGGTACCA
GCAGAAACCAGGACAGCCTCCTAAATTGCTCATTTACTGGGCATCTACGCGGGAGTCCGGGGTC
CCTGACCGATTCAGTGGCAGCGGGTCTGGGACAGATTTCACTCTGACCATCAGCAGCCTGCAGC
CTGAAGATGTGGCAGCATATTACTGTCAGCAATATTATAGGACTCCTATCACTTTCGGCCCTGG
GACCAAGGTGGAGATCAAACGAACTGTGGCG

TABLE 4

Amino acid sequence and nucleotide sequence of sample No. 42

<VH region: SEQ ID NO: 7>
GlnValGlnLeuValGluSerGlyAlaGluValArgLysProGlyAlaSerValLysValSerC
ysGlnAlaSerGlyTyrThrPheThrAspHisTyrLeuHisTrpLeuArgGlnAlaProGlyGl
nGlyLeuGluTrpMetGlyTrpIleAsnProAsnIleIleGluAlaArgTyrValAlaArgLys
PheArgGlySerValAsnLeuThrArgAspThrAlaIleGlnThrValTyrIleGluMetSerA
rgLeuThrSerAspAspThrAlaThrTyrPheCysAlaArgAlaLeuLysGluGlyGlyTyrSe
rTyrGlyTyrTyrAspHisTrpGlyProGlyThrLeuValThrValSerSerAla <VH region: SEQ ID NO: 15>
CAGGTGCAGCTGGTGGAGTCTGGGGCTGAGGTGAGGAAGCCTGGGGCCTCAGTGAAGGTCTCCT
GTCAGGCCTCTGGATACACCTTCACCGACCACTATCTCCACTGGCTGCGACAGGCCCCCGGACA
AGGGCTTGAGTGGATGGGGTGGATCAATCCCAACATCATTGAAGCCAGATACGTCGCACGGAAG
TTTAGAGGCAGTGTCAACCTGACCAGGGACACGGCCATCCAGACAGTGTACATAGAAATGAGCC
GCCTGACATCTGACGACACGGCCACCTACTTCTGTGCGAGAGCGTTAAAGGAGGGCGGATATAG
TTATGGTTATTACGACCATTGGGGCCCGGGAACCCTGGTCACTGTCTCCTCAGCG <VL region: SEQ ID NO: 8>
GluIleValMetThrGlnSerProCysProSerProLeuGluSerArgProProSerProAlaG
lyLeuValArgAlaSerTrpIleAlaMetMetAlaThrProIleTrpThrGlyThrCysArgSe
rGlnGlySerLeuHisSerSerSerIleTyrThrLeuSerHisArgAlaProGlyValProAsp
ArgPheSerGlySerGlySerGlyThrAspPheThrLeuLysIleSerArgValGluAlaGluA
spValGlyValTyrTyrCysLeuGlnArgIleAspPheProPheThrPheGlyProGlyThrLy
sValGluIleLysArgThrValAla <VL region: SEQ ID NO: 16>
GAAATTGTGATGACTCAGTCTCCCTGCCCGTCACCCCTGGAGAGCCGGCCTCCATCTCCTGCAG
GTCTAGTCAGAGCCTCTTGGATAGCGATGATGGCGACACCTATTTGGACTGGTACCTGCAGAAG
CCAGGGCAGTCTCCACAGCTCCTCGATCTATACCCTTTCCCATCGGGCCCCTGGAGTCCCAGAC
AGGTTCAGTGGCAGTGGGTCAGGCACTGATTTCACACTGAAAATCAGCAGGGTGGAGGCTGAGG
ATGTTGGAGTTTATTACTGCCTGCAACGTATAGACTTTCCATTCACTTTCGGCCCAGGGACCAA
GGTGGAAATCAAACGAACTGTGGCG By using the sequence information obtained of the scFvs of the samples, human IgGs were then prepared by gene recombination techniques. Expression plasmid vectors "pHIgHzeo" and "pHIgKneo" shown in the plasmid maps in FIGS. 1A and 1B, respectively, were used. Full nucleotide sequences of pHIgHzeo and pHIgKneo are shown in SEQ ID NOs: 17 and 18, respectively.

Figure 1B:
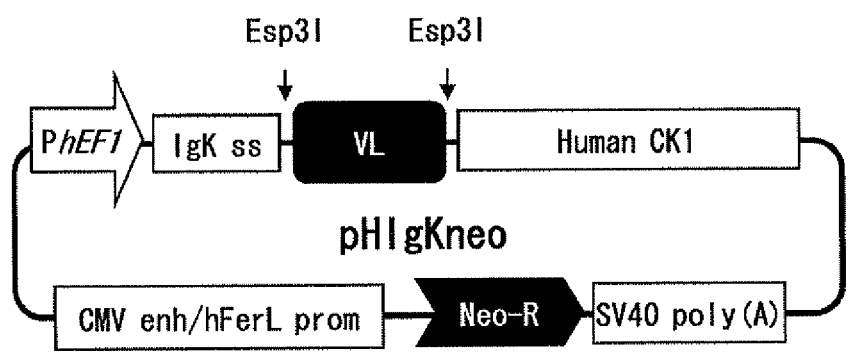
FIG. 1B is a plasmid map depicting an overview of an expression plasmid vector "pHIgKneo"

As shown in the plasmid map in FIG. 1A, pHIgHzeo contains genes (CH1 to CH3) encoding the human IgG1 heavy chain constant region (CH region). On the other hand, as shown in the plasmid map in FIG. 1B, pHIgKneo contains a gene (CK1) encoding the human IgG1 light chain (κ chain) constant region (CL region). These plasmid vectors have, as shown in the figures, two cleavage sites for the restriction enzyme Esp3I (recognition sites of Esp3I are agagacg at positions 619 to 625 and gtctcg at positions 2336 to 2341 of SEQ ID NO: 17; and gagacg at positions 622 to 627 and gtctcg at positions 2319 to 2324 of SEQ ID NO: 18), so that a nucleotide sequence encoding the amino acid sequence of the VH region of interest (hereinafter referred to as "VH coding gene") or a nucleotide sequence encoding the amino acid sequence of the VL region (hereinafter referred to as "VL coding gene") can be inserted at the site(s) (cleavage site(s)) cleaved after treatment with Esp3I.

Specifically, to 50 ng of each plasmid vector treated with the enzyme Esp3I was added 10 ng of the VH coding gene and VL coding gene of any of the samples respectively and a recombinant pHIgHzeo in which the VH coding gene of interest (i.e., any nucleotide sequence of SEQ ID NO: 9, 11, 13 or 15) is incorporated at the Esp3I cleavage site was obtained by using commercially available In-Fusion Advantage PCR Cloning Kit (Clontech) according to the instruction of the product. In the similar manner, a recombinant pHIgK-neo in which the VL coding gene of interest (i.e., a nucleotide sequence of SEQ ID NO: 10, 12, 14 or 16) is incorporated at the Esp3I cleavage site was obtained.

The obtained recombinant expression vectors were introduced in general competent cells, *Escherichia coli* TOP10 competent cells, and transformants were selected on 10% sucrose-containing SOB medium plates added zeocin or kanamycin at the concentration of 50 μg/mL.

In order to obtain positive clones in which desired genes (inserts) were correctly fused, i.e., to obtain VH recombinant pHIgHzeo and VL recombinant pHIgKneo, colony PCR was carried out with two sets of primers, i.e., a set of pFUSEseq-f and CHseq-r represented by SEQ ID NOs: 19 and 20, respectively, for VH and a set of IgKss-f and Ckseq-r represented by SEQ ID NOs: 21 and 22, respectively, for VL, and the inserts were verified.

The positive clones (*E. coli* TOP10) in which the inserts were correctly fused were isolated and grown on the 10% sucrose-containing SOB medium.

Among the thus obtained recombinant expression vectors, the VH recombinant pHigHzeo and VL recombinant pHIgK-neo which correctly corresponded to the samples of interest (Nos. 45, 38, 40 and 42) were mixed in equal amount and introduced into commercially available FreeStyle™ CHO-S cells (Invitrogen), which were then cultured according to the conventional manner to produce divalent antibodies, complete human IgGs (hIgGs). The obtained IgGs corresponding to avobe four say samples are designated as hIgG45, hIgG38, hIgG40 and hIgG42 by using the sample numbers.

TEST EXAMPLE 2

Verification of Epitope Located Region

The thus obtained four artificially produced anti-EGFR antibodies (human IgGs) were studied for EGFR binding portions.

Namely, four different genes encoding EGFR extracellular domain deletion mutant peptides in which one of four subdomains (L1, C1, L2 and C2) was deleted from the EGFR extracellular domain were prepared by PCR using appropriate primers. The gene encoding the EGFR extracellular domain peptide without deletion was also prepared.

The expression virus vectors containing the above genes were constructed and used to transfect BJ cells in order to obtain BJ cells which express the EGFR extracellular domain deletion mutant peptides or the EGFR extracellular domain peptide without deletion.

Figure 2:
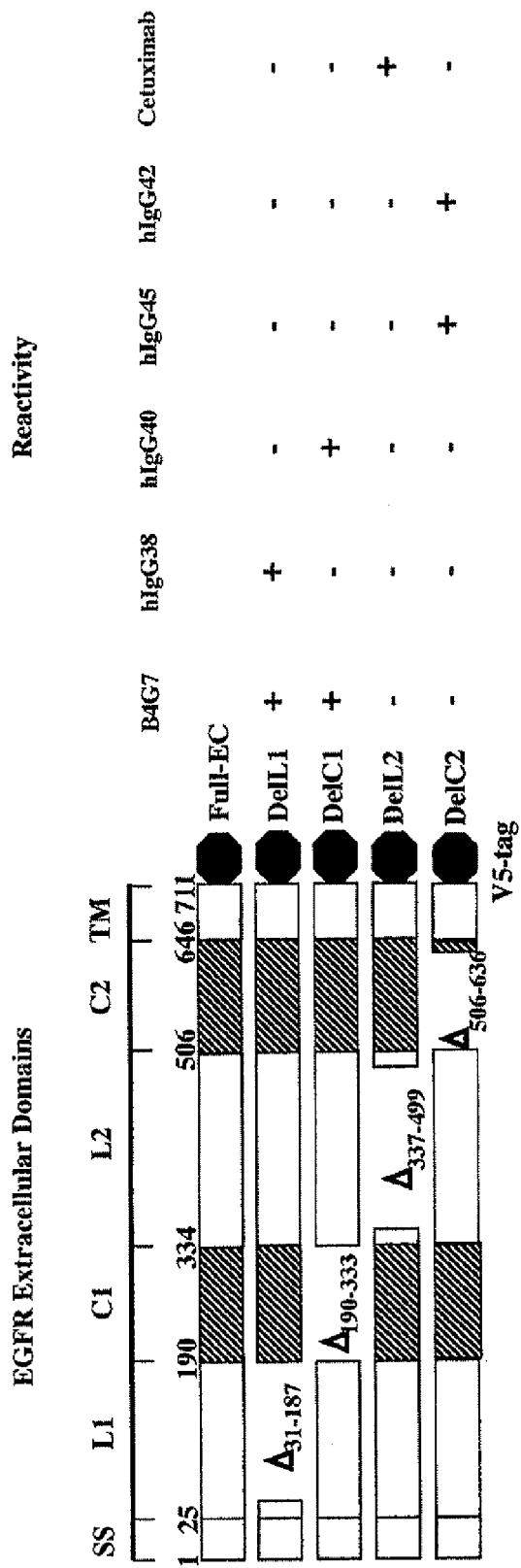
FIG. 2 is a drawing showing deleted parts of EGFR extracellular domain deletion mutant peptide obtained in Test Example (left) and binding parts of test antibodies (right)

FIG. 2 shows on its left side deleted parts of EGFR extracellular domain deletion mutant peptides. The portions shown with Δ in this figure are the deleted parts (the numbers denote the positions and regions of deleted amino acid residues from the N-terminal). As shown in this figure, all of the EGFR extracellular domain peptides constructed in this Test Example have a signal sequence (SS) on the N-terminal side and an EGFR transmembrane domain (TM) on the C-terminal side which is provided with the V5-tag on the C-terminal side thereof.

Accordingly, the EGFR extracellular domain deletion mutant peptides or the EGFR extracellular domain peptide without deletion expressed in BJ cells together with hIgG45, hIgG38, hIgG40 and hIgG42 obtained in Test Example 1 and commercially available anti-EGFR monoclonal antibodies "B4G7" and "cetuximab" as controls were used in conventional Western blot analysis.

By comparative analysis of binding capacity of test antibodies to test peptides in this Western blotting, i.e., by analyzing which subdomain among four subdomains forming the extracellular domain was deleted at the time of loss of the binding capacity, the portions to which test antibodies bind were elucidated as shown on the right side of FIG. 2. The test antibodies with "+" on the right side of FIG. 2 bind to the deleted subdomains shown in the corresponding rows in the left side of FIG. 2.

Namely, as apparent from the results shown in FIG. 2, it was verified that hIgG45, hIgG38, hIgG40 and hIgG42 obtained in Test Example 1 have binding portions (epitopes) in C2, L1, C1 and C2 domains, respectively.

TEST EXAMPLE 3

Evaluation of Cell Growth Suppression (Inhibition) Capacity of Anti-EGFR Antibodies (1)

The obtained antibodies were provided to various cultured cells and the cell growth suppression (inhibition) capacities thereof were evaluated in an in vitro cell culture test. The cell lines used are four, which are known A431, A549, NA and MDA-MB-231. Namely, A431 is a human squamous cell carcinoma cell line, A549 is a human lung squamous cell carcinoma cell line, NA is a human oral squamous cell carcinoma cell line and MDA-M13-231 is a human breast cancer cell line.

Specifically, the antibody at a predetermined concentration was added to the above cell line with using "AlamarBlue®" (Invitrogen) which is a dye for cell growth evaluation and the degree of cell growth after a predetermined culture time (24, 48 or 72 hours) was measured as the OD value of the above dye.

Namely, cells were seeded in wells of a 96-well plate containing the DMEM medium containing 10% FCS at the cell concentration of $1 \times 10^4$ cells/well and incubated under 37° C., 5% $CO_2$ for 2 days until the mid-log phase. The medium was exchanged with the FCS-free DMEM medium (free from phenol red in order to avoid the affect from the color of the medium) and the incubation was continued for further overnight. The medium was then exchanged with the DMEM medium containing 0.1% FCS, any of the test antibodies was added at a predetermined concentration (0.1 μg/mL or 10 μg/mL) and the incubation was continued. Controls were the one without antibody and the one added with the B4G7 antibody at the same concentration. The dye AlamarBlue® was added so as to obtain the final concentration of 10% per well.

Figure 3:
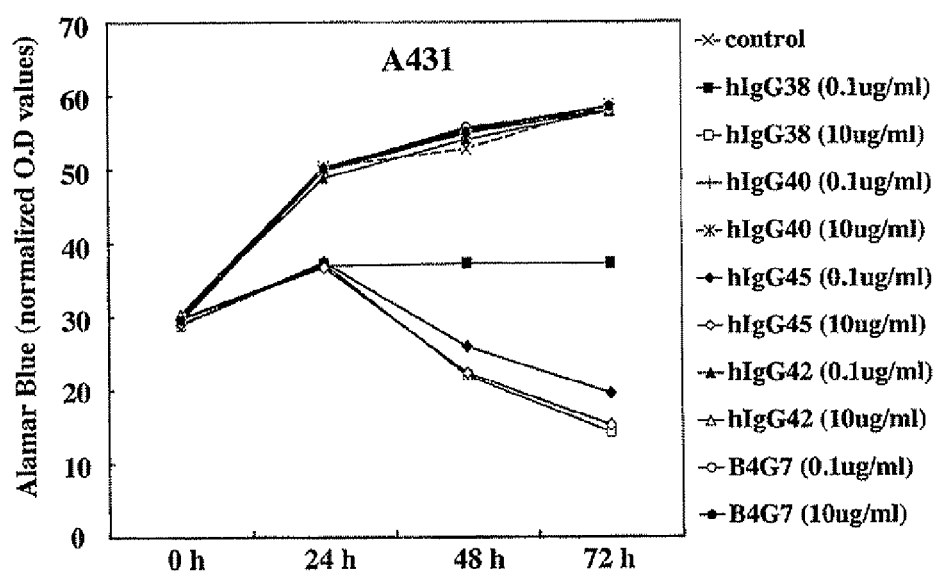
FIG. 3 is a graph of the results of AlamarBlue® assay showing effects of test antibodies on growth of the A431 cell line over time.
Figure 4:
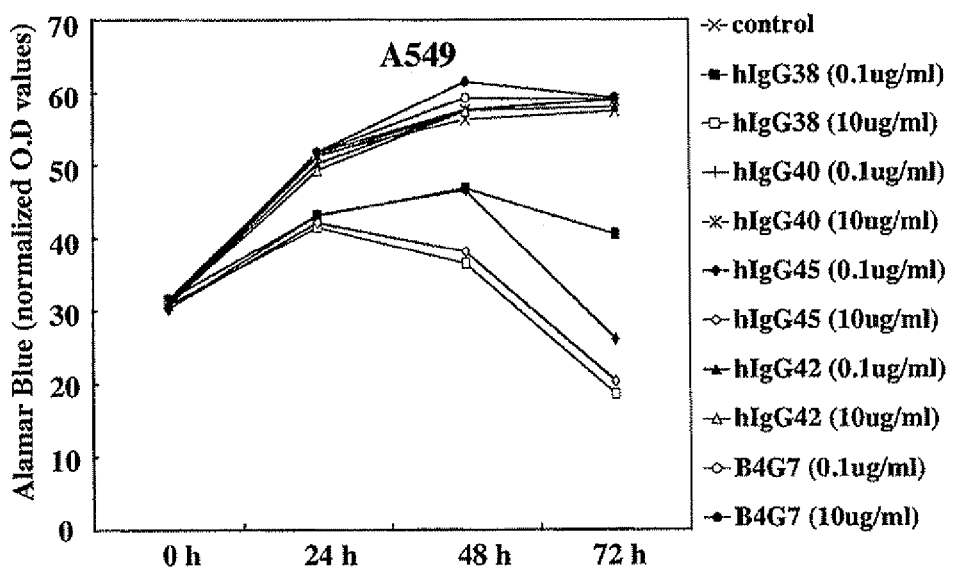
FIG. 4 is a graph of the results of AlamarBlue® assay showing effects of test antibodies on growth of the A549 cell line over time.
Figure 5:
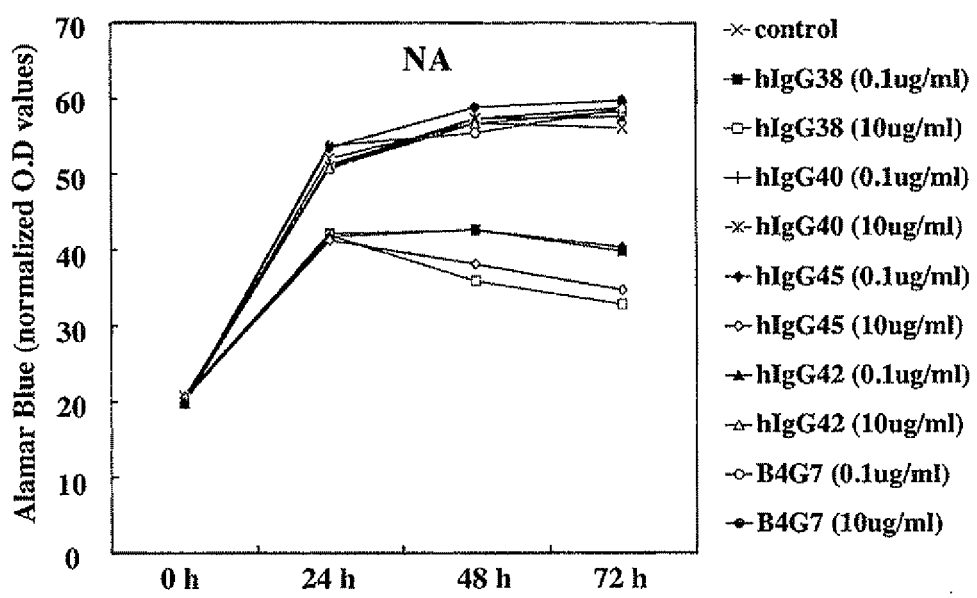
FIG. 5 is a graph of the results of AlamarBlue® assay showing effects of test antibodies on growth of the NA cell line over time.
Figure 6:
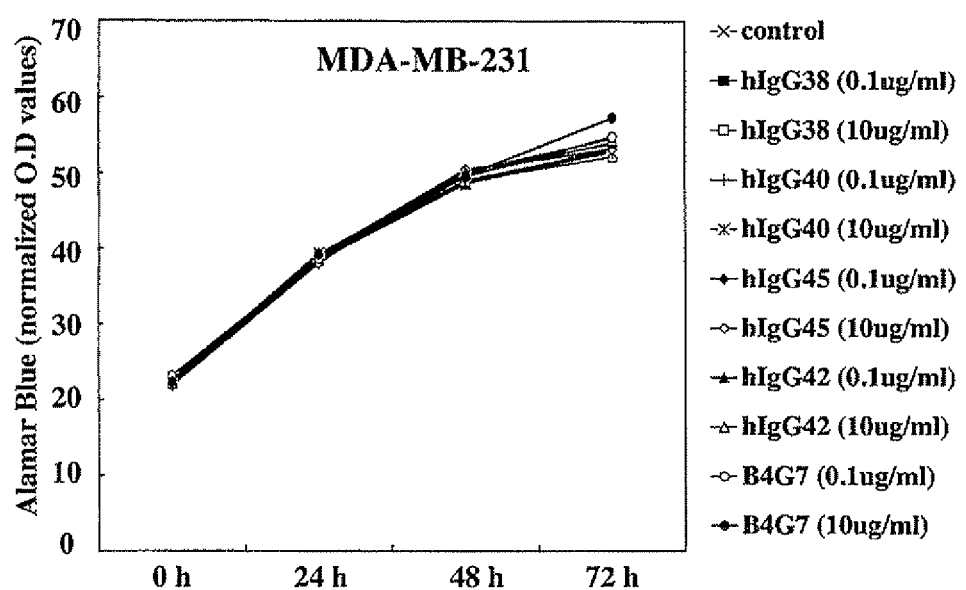
FIG. 6 is a graph of the results of AlamarBlue® assay showing effects of test antibodies on growth of the MDA-MB-231 cell line over time.

At 24, 48 and 72 hours after addition of the antibody, absorbance was measured at 570 nm and 600 nm with a conventional spectrophotometer. The results are shown in FIG. 3 (A431 cell line), FIG. 4 (A549 cell line), FIG. 5 (NA cell line) and FIG. 6 (MDA-MB-231 cell line). As apparent from these graphs, it was found that IgG45 and IgG38 have significant cell growth suppression (inhibition) effect on A431, A549 and NA cell lines which express EGFR at a relatively high rate. Particularly, high cell growth suppression (inhibition) effect was found against the A549 cell line which derives from KRAS mutant malignant tumor cells. FIG. 2 shows that IgG42 and IgG45 had different reactivity against the cell lines as described above, which otherwise bound to the same portion (i.e., the C2 domain) in appearance. The reason for this is believed that actual epitopes for IgG42 and IgG45 are in two different narrower portions in the C2 domain. This shows that IgG45 and/or IgG38 can act as effective antibody drugs against KRAS mutant malignant tumors such as A549 for which the effect by conventional anti-EGFR antibodies (e.g., B4G7 used as the control in the present Test Example) could not be seen.

TEST EXAMPLE 4

Evaluation of Cell Growth Suppression (Inhibition) Capacity of Anti-EGFR Antibodies (2)

Next, in order to study the concentration (dose) dependency of cell growth suppression capacity of the test antibodies, the AlamarBlue® assay was carried out as described above and cell viability (%) at respective concentrations (0.1, 1, 10 and 100 µg/mL) of the antibodies was evaluated.

The cell lines used were A549 and NA as described above as well as SK-OV3 (human ovarian carcinoma cell line), HCT-116 (human colon cancer cell line) and Caki-2 (human renal carcinoma cell line).

The absorbance was measured at 72 hours after addition of the antibody at a predetermined amount under the culture conditions described in Test Example 3. Cell viability (%) was calculated according to the following formula:

Viability(%)=[(*OD* standard value for treatment without antibody−*OD* standard value for treatment with IgG)/*OD* standard value for treatment without antibody]×100.

Figure 7:
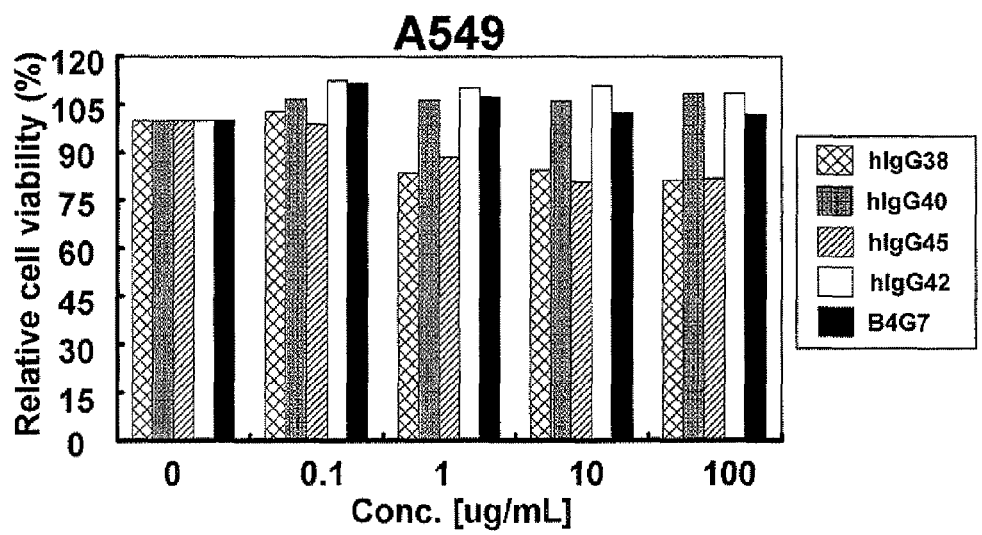
FIG. 7 is a graph of the results of AlamarBlue® assay showing effects of different concentrations (0.1, 1, 10, 100 μg/mL) of test antibodies on growth of the A549 cell line.
Figure 8:
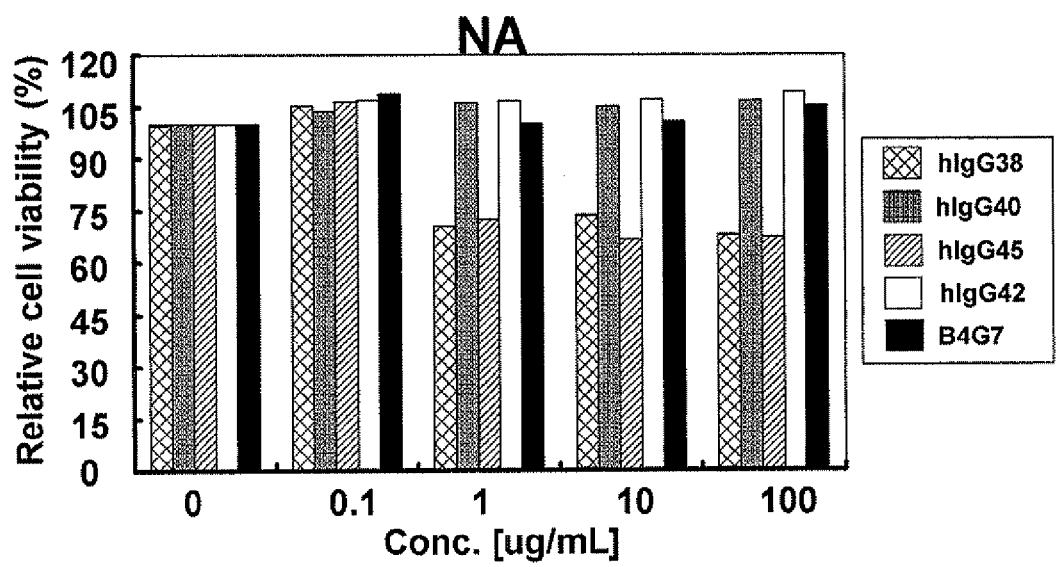
FIG. 8 is a graph of the results of AlamarBlue® assay showing effects of different concentrations (0.1, 1, 10, 100 μg/mL) of test antibodies on growth of the NA cell line.
Figure 9:
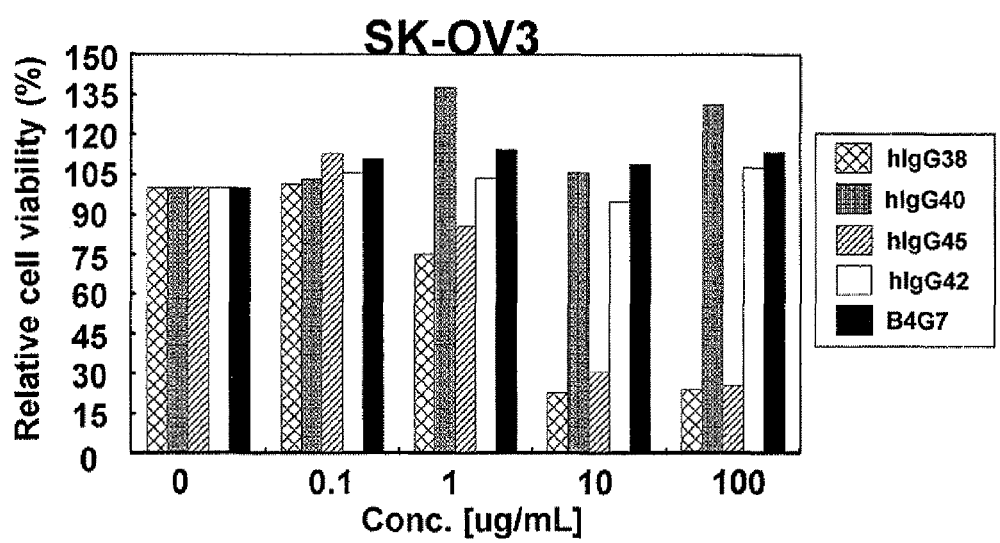
FIG. 9 is a graph of the results of AlamarBlue® assay showing effects of different concentrations (0.1, 1, 10, 100 μg/mL) of test antibodies on growth of the SK-OV3 cell line.
Figure 10:
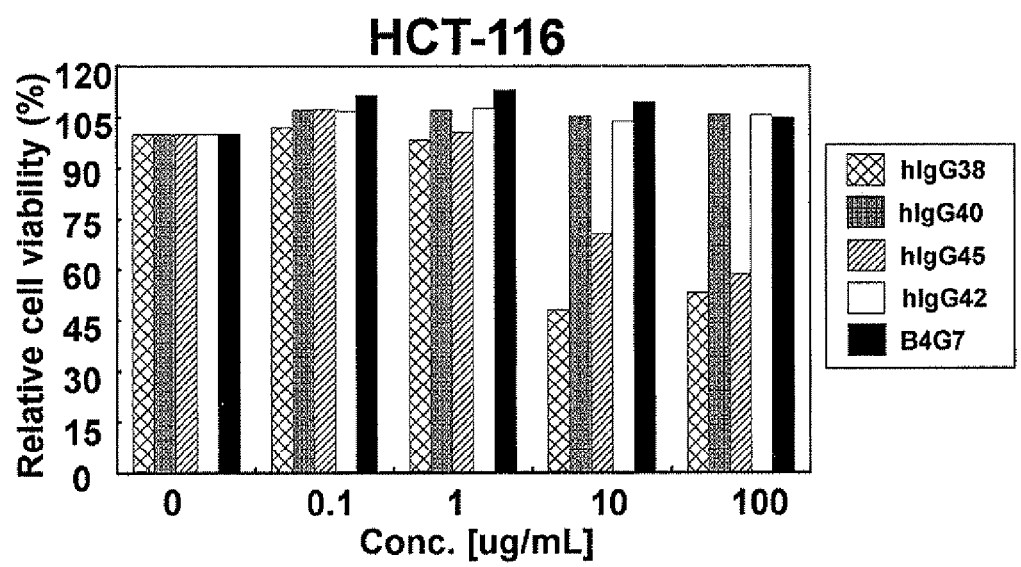
FIG. 10 is a graph of the results of AlamarBlue® assay showing effects of different concentrations (0.1, 1, 10, 100 μg/mL) of test antibodies on growth of the HCT-116 cell line.
Figure 11:
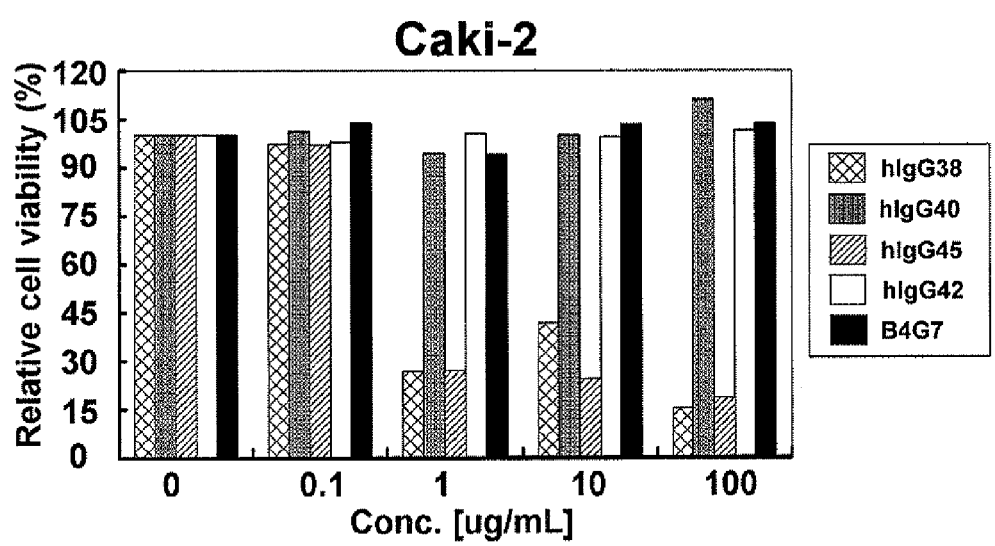
FIG. 11 is a graph of the results of AlamarBlue® assay showing effects of different concentrations (0.1, 1, 10, 100 μg/mL) of test antibodies on growth of the Caki-2 cell line.

The results are shown in FIG. 7 (A549 cell line), FIG. 8 (NA cell line), FIG. 9 (SK-OV3 cell line), FIG. 10 (HCT-116 cell line) and FIG. 11 (Caki-2 cell line).

As apparent from these graphs, it was found that, among the antibodies tested, IgG45 and IgG38 can stably (typically, at a concentration of 1 µg/mL or more, particularly a concentration of 10 µg/mL or more) show significant cell growth suppression (inhibition) effect against malignant tumor cells which express EGFR at a relatively high rate and in which the KRAS gene is mutated.

Suitable examples of useful anti-EGFR antibodies (i.e., IgG45 and IgG38) provided by the present invention have been described by way of the above Test Examples. However, the present invention is not limited to these embodiments. For example, Fab and F(ab')$_2$ fragments obtained by conventional enzyme treatment of the above complete human IgG45 and complete human IgG38 are typical examples encompassed by the present antibodies.

Industrial Applicability

As described above, the anti-EGFR antibodies disclosed herein have high cell growth suppression (inhibition) activity particularly against malignant tumor cells (high EGFR expressing cells) in which the KRAS gene is mutated, and therefore the cell growth inhibitor containing the antibodies can be used as the composition for medicines such as anticancer drugs.

[Sequence Listing Free Text]

SEQ ID NOs: 1 to 8: Synthetic peptides
SEQ ID NOs: 9, 11, 13 and 15: Variable regions of the heavy chain for artificial IgG
SEQ ID NOs: 10, 12, 14 and 16: Variable regions of the light chain for artificial IgG
SEQ ID NOs: 17 and 18: Plasmid DNAs
SEQ ID NOs: 19 to 22: Primers

The invention claimed is:

1. A composition comprising:
  (1) a pharmaceutically acceptable carrier; and
  (2) an active ingredient capable of suppressing growth of at least one epidermal growth factor receptor (EGFR)-expressing cell, the active ingredient comprising either or both of
    (A) an anti-EGFR antibody having specific binding capacity to EGFR, including:
      a heavy chain variable region (VH region) having the amino acid sequence of SEQ ID NO: 1, and
      a light chain variable region (VL region) having the amino acid sequence of SEQ ID NO: 2, wherein:
      the anti-EGFR antibody has specific binding capacity to an epitope of EGFR,
      the epitope is in a cysteine-rich subdomain 2 (C2) being a fourth subdomain from a N-terminal of an extracellular domain among four subdomains contained in EGFR; and
    (B) an anti-EGFR antibody having specific binding capacity to EGFR, including:
      a heavy chain variable region (VH region) having the amino acid sequence of SEQ ID NO: 3, and
      a light chain variable region (VL region) having an-the amino acid sequence of SEQ ID NO: 4, wherein:
      the anti-EGFR antibody has specific binding capacity to an epitope of EGFR,
      the epitope is in a ligand-binding domain 1 (L1) being a first subdomain from a N-terminal of an extracellular domain among four subdomains contained in EGFR.

2. The composition of claim 1, wherein at least one of the antibody (A) and the antibody (B) further comprises a heavy chain constant region (CH region) and a light chain constant region (CL region) of human IgG in addition to the VH region and the VL region, and has a form of human IgG.

3. The composition of claim 1, wherein the EGFR-expressing cell is a KRAS mutant malignant tumor cell and the composition suppresses growth of the KRAS mutant malignant tumor cell.

4. An anti-EGFR antibody having specific binding capacity to epidermal growth factor receptor (EGFR), comprising:
  a heavy chain variable region (VH region) having the amino acid sequence of SEQ ID NO: 1; and
  a light chain variable region (VL region) having the amino acid sequence of SEQ ID NO: 2;
  wherein:
  the anti-EGFR antibody has specific binding capacity to an epitope of EGFR, and
  the epitope is in a cysteine-rich subdomain 2 (C2) being a fourth subdomain from a N-terminal of an extracellular domain among four subdomains contained in EGFR.

5. An anti-EGFR antibody having specific binding capacity to epidermal growth factor receptor (EGFR), comprising:
  a heavy chain variable region (VH region) having the amino acid sequence of SEQ ID NO: 3; and
  a light chain variable region (VL region) having the amino acid sequence of SEQ ID NO: 4;
  wherein:
  the anti-EGFR antibody has specific binding capacity to an epitope of EGFR, and
  the epitope is in a ligand-binding domain 1 (L1) being a first domain from a N-terminal of a extracellular domain among four subdomains contained in EGFR.

6. The anti-EGFR antibody of claim 4, further comprising a heavy chain constant region (CH region) and a light chain constant region (CL region) of human IgG in addition to the VH region and the VL region, and having a form of human IgG.

7. A method for suppressing a cell growth, comprising:
applying the anti-EGFR antibody of claim 4 to at least one target epidermal growth factor receptor (EGFR)-expressing cell so as to suppress growth of the EGFR-expressing cell.

8. The method of claim 7, wherein the EGFR expressing cell is a KRAS mutant malignant tumor cell and the growth of the KRAS mutant malignant tumor cell is suppressed.

9. A method for treating a patient with an anti-EGFR antibody in need thereof, comprising the step of:
administering to the patient the composition of claim 1 in an effective amount to suppress growth of EGFR-expressing cells.

* * * * *

SEQUENCE LISTING

```
<160> NUMBER OF SEQ ID NOS: 22

<210> SEQ ID NO 1
<211> LENGTH: 121
<212> TYPE: PRT
<213> ORGANISM: Artificial sequence
<220> FEATURE:
<223> OTHER INFORMATION: Synthetic construct - Synthetic peptide

<400> SEQUENCE: 1

Gln Val Gln Leu Gln Glu Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Ser His Ser Gly Ser Thr Gly Tyr Asn Pro Ser Leu Lys
    50                  55                  60

Ser Arg Val Ala Ile Ser Val Asp Thr Pro Lys Asn Gln Phe Ser Leu
65                  70                  75                  80

Lys Leu Asn Ser Val Thr Ala Ala Asp Thr Ala Leu Tyr Tyr Cys Ala
                85                  90                  95

Arg Leu Thr Thr Val Val Gly Gly Asn Trp Phe Asp Pro Trp Gly Gln
            100                 105                 110

Gly Thr Leu Val Thr Val Ser Ser Ala
        115                 120

<210> SEQ ID NO 2
```

<211> LENGTH: 114
<212> TYPE: PRT
<213> ORGANISM: Artificial sequence
<220> FEATURE:
<223> OTHER INFORMATION: Synthetic construct - Synthetic peptide

<400> SEQUENCE: 2

```
Gln Ser Val Leu Thr Gln Pro Pro Ser Ala Ser Gly Thr Pro Gly Gln
1               5                   10                  15

Gly Val Thr Ile Ser Cys Ser Gly Ser Ser Ala Asp Ile Gly Ala Asn
            20                  25                  30

Tyr Val Tyr Trp Tyr Gln Gln Leu Pro Gly Thr Ala Pro Lys Leu Leu
        35                  40                  45

Ile Tyr Ser Ile Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Gly Gly Trp Ala Phe Gly Gly Gly Thr Lys Val Glu Ile Lys Arg Thr
            100                 105                 110

Val Ala
```

<210> SEQ ID NO 3
<211> LENGTH: 125
<212> TYPE: PRT
<213> ORGANISM: Artificial sequence
<220> FEATURE:
<223> OTHER INFORMATION: Synthetic construct - Synthetic peptide

<400> SEQUENCE: 3

```
Gln Val Gln Leu Gln Glu Ser Gly Pro Gly Leu Val Lys Pro Ser Glu
1               5                   10                  15

Thr Val Ser Leu Thr Cys Ser Val Ser Gly Asp Ser Leu Ser His Asn
            20                  25                  30

Tyr Trp Ser Trp Ile Arg Gln Pro Pro Gly Lys Gly Leu Glu Trp Ile
        35                  40                  45

Gly Tyr Ile Tyr Pro Ser Gly Thr Ser Gly Thr Thr Lys Tyr Asn Pro
    50                  55                  60

Ser Leu Lys Ser Arg Val Thr Ile Ser Ser Asp Thr Ser Lys Asn Gln
65                  70                  75                  80

Phe Ser Leu Arg Leu Thr Ser Val Thr Ala Ala Asp Thr Ala Ile Tyr
                85                  90                  95

Tyr Cys Ala Lys Glu Ala Ile Thr Ala Asn Ala Trp Pro Val Ser Asp
            100                 105                 110

Tyr Trp Gly Gln Gly Thr Leu Val Thr Val Ser Ser Ala
        115                 120                 125
```

<210> SEQ ID NO 4
<211> LENGTH: 111
<212> TYPE: PRT
<213> ORGANISM: Artificial sequence
<220> FEATURE:
<223> OTHER INFORMATION: Synthetic construct - Synthetic peptide

<400> SEQUENCE: 4

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
```

```
                    20                  25                  30

Leu Ala Trp Phe Gln Gln Lys Pro Gly Gln Ala Pro Arg Leu Leu Ile
                35                  40                  45

Tyr Asp Ala Ser Asn Arg Ala Thr Gly Val Pro Ala Arg Phe Ser Gly
            50                  55                  60

Ser Gly Ser Gly Thr Asp Phe Thr Leu Thr Ile Ser Leu Glu Pro
65                  70                  75                  80

Glu Asp Phe Ala Val Tyr Tyr Cys Gln Gln Arg Gly Asp Trp Pro Leu
                85                  90                  95

Thr Phe Gly Gly Gly Thr Lys Val Glu Ile Lys Arg Thr Val Ala
                100                 105                 110

<210> SEQ ID NO 5
<211> LENGTH: 123
<212> TYPE: PRT
<213> ORGANISM: Artificial sequence
<220> FEATURE:
<223> OTHER INFORMATION: Synthetic construct - Synthetic peptide

<400> SEQUENCE: 5

Gln Val Gln Leu Val Gln Ser Gly Pro Gly Leu Val Lys Pro Ser Glu
1               5                   10                  15

Thr Leu Ser Leu Thr Cys Thr Val Ser Gly Gly Ser Val Ser Ser Gly
                20                  25                  30

Thr Tyr Cys Trp Ser Trp Ile Arg Gln Pro Pro Gly Lys Gly Leu Glu
                35                  40                  45

Trp Ile Ala Tyr Ile Cys Asn Ser Gly Ser Thr Ser Tyr Asn Pro Ser
            50                  55                  60

Leu Lys Ser Arg Gly Thr Ile Ser Val Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Leu Ser Leu Ile Met Val Tyr His Ile Phe Asp Tyr Trp
                100                 105                 110

Gly Gln Gly Thr Leu Val Thr Val Ser Ser Ala
            115                 120

<210> SEQ ID NO 6
<211> LENGTH: 117
<212> TYPE: PRT
<213> ORGANISM: Artificial sequence
<220> FEATURE:
<223> OTHER INFORMATION: Synthetic construct - Synthetic peptide

<400> SEQUENCE: 6

Asp Ile Val Met Thr Gln Thr Pro Asp Ser Leu Ala Val Ser Leu Gly
1               5                   10                  15

Glu Arg Ala Thr Ile Asn Cys Lys Ser Ser Gln Asn Leu Leu Tyr Thr
                20                  25                  30

Ser Ser Asn Gln Thr Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
            50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Val Ala Ala Tyr Tyr Cys Gln Gln
                85                  90                  95
```

```
Tyr Tyr Arg Thr Pro Ile Thr Phe Gly Pro Gly Thr Lys Val Glu Ile
            100                 105                 110

Lys Arg Thr Val Ala
        115

<210> SEQ ID NO 7
<211> LENGTH: 125
<212> TYPE: PRT
<213> ORGANISM: Artificial sequence
<220> FEATURE:
<223> OTHER INFORMATION: Synthetic construct - Synthetic peptide

<400> SEQUENCE: 7

Gln Val Gln Leu Val Glu Ser Gly Ala Glu Val Arg Lys Pro Gly Ala
1               5                   10                  15

Ser Val Lys Val Ser Cys Gln Ala Ser Gly Tyr Thr Phe Thr Asp His
            20                  25                  30

Tyr Leu His Trp Leu Arg Gln Ala Pro Gly Gln Gly Leu Glu Trp Met
        35                  40                  45

Gly Trp Ile Asn Pro Asn Ile Ile Glu Ala Arg Tyr Val Ala Arg Lys
    50                  55                  60

Phe Arg Gly Ser Val Asn Leu Thr Arg Asp Thr Ala Ile Gln Thr Val
65                  70                  75                  80

Tyr Ile Glu Met Ser Arg Leu Thr Ser Asp Asp Thr Ala Thr Tyr Phe
                85                  90                  95

Cys Ala Arg Ala Leu Lys Glu Gly Gly Tyr Ser Tyr Gly Tyr Tyr Asp
            100                 105                 110

His Trp Gly Pro Gly Thr Leu Val Thr Val Ser Ser Ala
        115                 120                 125

<210> SEQ ID NO 8
<211> LENGTH: 115
<212> TYPE: PRT
<213> ORGANISM: Artificial sequence
<220> FEATURE:
<223> OTHER INFORMATION: Synthetic construct - Synthetic peptide

<400> SEQUENCE: 8

Glu Ile Val Met Thr Gln Ser Pro Cys Pro Ser Leu Glu Ser Arg
1               5                   10                  15

Pro Pro Ser Pro Ala Gly Leu Val Arg Ala Ser Trp Ile Ala Met Met
            20                  25                  30

Ala Thr Pro Ile Trp Thr Gly Thr Cys Arg Ser Gln Gly Ser Leu His
        35                  40                  45

Ser Ser Ser Ile Tyr Thr Leu Ser His Arg Ala Pro Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Leu Gln Arg Ile
                85                  90                  95

Asp Phe Pro Phe Thr Phe Gly Pro Gly Thr Lys Val Glu Ile Lys Arg
            100                 105                 110

Thr Val Ala
        115

<210> SEQ ID NO 9
<211> LENGTH: 363
<212> TYPE: DNA
<213> ORGANISM: Artificial sequence
```

<220> FEATURE:
<221> NAME/KEY: CDS
<222> LOCATION: (1)..(363)
<223> OTHER INFORMATION: Synthetic construct -
      variable region of the heavy chain for artificial IgG

<400> SEQUENCE: 9

```
cag gtg cag ctg cag gag tgg ggc gca gga ctg ttg aag cct tcg gag      48
Gln Val Gln Leu Gln Glu Trp Gly Ala Gly Leu Leu Lys Pro Ser Glu
1               5                   10                  15 acc ctg tcc ctc acc tgc gct gtg tac ggt ggg tcc ttc agt gat tac      96
Thr Leu Ser Leu Thr Cys Ala Val Tyr Gly Gly Ser Phe Ser Asp Tyr
                20                  25                  30 tac tgg agc tgg atc cgg cag ccc cca ggg aag ggg ctg gag tgg atc     144
Tyr Trp Ser Trp Ile Arg Gln Pro Pro Gly Lys Gly Leu Glu Trp Ile
            35                  40                  45 gga gaa atc agt cat agc gga agt acc ggc tac aac ccg tcc ctc aag     192
Gly Glu Ile Ser His Ser Gly Ser Thr Gly Tyr Asn Pro Ser Leu Lys
        50                  55                  60 agt cga gtc gcc ata tca gtt gac acg ccc aag aac cag ttc tcc ctg     240
Ser Arg Val Ala Ile Ser Val Asp Thr Pro Lys Asn Gln Phe Ser Leu
65                  70                  75                  80 aag ctg aac tct gtg acc gcc gcg gac acg gct cta tat tat tgt gcg     288
Lys Leu Asn Ser Val Thr Ala Ala Asp Thr Ala Leu Tyr Tyr Cys Ala
                85                  90                  95 aga ctg aca aca gtg gtt ggg ggc aac tgg ttc gac ccc tgg ggc cag     336
Arg Leu Thr Thr Val Val Gly Gly Asn Trp Phe Asp Pro Trp Gly Gln
                100                 105                 110 gga acc ctg gtc acc gtc tcc tca gcg                                  363
Gly Thr Leu Val Thr Val Ser Ser Ala
            115                 120
```

<210> SEQ ID NO 10
<211> LENGTH: 342
<212> TYPE: DNA
<213> ORGANISM: Artificial sequence
<220> FEATURE:
<221> NAME/KEY: CDS
<222> LOCATION: (1)..(342)
<223> OTHER INFORMATION: Synthetic construct -
      variable region of the light chain for artificial IgG

<400> SEQUENCE: 10

```
cag tct gtt ctg act cag ccc cct tcc gcg tct ggg acc ccc ggg cag      48
Gln Ser Val Leu Thr Gln Pro Pro Ser Ala Ser Gly Thr Pro Gly Gln
1               5                   10                  15 ggg gtc acc atc tct tgt tct gga agc agt gcc gac atc gga gca aat      96
Gly Val Thr Ile Ser Cys Ser Gly Ser Ser Ala Asp Ile Gly Ala Asn
                20                  25                  30 tat gta tac tgg tac cag caa ctt cca gga acg gcc ccc aaa ctc ctc     144
Tyr Val Tyr Trp Tyr Gln Gln Leu Pro Gly Thr Ala Pro Lys Leu Leu
            35                  40                  45 atc tat tct att aat cag cgg ccc tca ggg gtc cct gac cga ttc tct     192
Ile Tyr Ser Ile Asn Gln Arg Pro Ser Gly Val Pro Asp Arg Phe Ser
        50                  55                  60 ggc tcc aag tct ggc acc tca gcc tcc ctg gcc atc agt ggg ctc cgg     240
Gly Ser Lys Ser Gly Thr Ser Ala Ser Leu Ala Ile Ser Gly Leu Arg
65                  70                  75                  80 tcc gag gat gag gct gat tat tac tgt gca aca tgg gat gac agc ctg     288
Ser Glu Asp Glu Ala Asp Tyr Tyr Cys Ala Thr Trp Asp Asp Ser Leu
                85                  90                  95 ggt ggc tgg gca ttc ggc gga ggg acc aag gtg gaa atc aaa cga act     336
Gly Gly Trp Ala Phe Gly Gly Gly Thr Lys Val Glu Ile Lys Arg Thr
```

```
                    100                 105                 110
gtg gcg                                                                      342
Val Ala
```

<210> SEQ ID NO 11
<211> LENGTH: 375
<212> TYPE: DNA
<213> ORGANISM: Artificial sequence
<220> FEATURE:
<221> NAME/KEY: CDS
<222> LOCATION: (1)..(375)
<223> OTHER INFORMATION: Synthetic construct -
      variable region of the heavy chain for artificial IgG

<400> SEQUENCE: 11

```
cag gtg cag cta cag gag tcg ggc cca gga ctg gtg aag cct tcg gag           48
Gln Val Gln Leu Gln Glu Ser Gly Pro Gly Leu Val Lys Pro Ser Glu
1               5                   10                  15 acc gtg tcc ctc acc tgc agt gtc tct ggt gac tcc ctc agt cat aac           96
Thr Val Ser Leu Thr Cys Ser Val Ser Gly Asp Ser Leu Ser His Asn
            20                  25                  30 tac tgg agt tgg atc cgg cag cca cca ggg aag gga ctg gag tgg att          144
Tyr Trp Ser Trp Ile Arg Gln Pro Pro Gly Lys Gly Leu Glu Trp Ile
        35                  40                  45 ggg tat atc tat cct agt ggg act agt ggg acc acc aag tac aat ccc          192
Gly Tyr Ile Tyr Pro Ser Gly Thr Ser Gly Thr Thr Lys Tyr Asn Pro
    50                  55                  60 tcc ctc aag agt cga gtc acc ata tca agc gac acg tcc aag aac cag          240
Ser Leu Lys Ser Arg Val Thr Ile Ser Ser Asp Thr Ser Lys Asn Gln
65                  70                  75                  80 ttc tcc ctg agg ttg acc tct gtg acc gct gcg gac acg gcc ata tat          288
Phe Ser Leu Arg Leu Thr Ser Val Thr Ala Ala Asp Thr Ala Ile Tyr
                85                  90                  95 tat tgt gcg aaa gag gca atc acc gcc aat gcc tgg ccg gtg tcg gac          336
Tyr Cys Ala Lys Glu Ala Ile Thr Ala Asn Ala Trp Pro Val Ser Asp
            100                 105                 110 tac tgg ggc cag gga acc ctg gtc acc gtc tcc tca gcg                      375
Tyr Trp Gly Gln Gly Thr Leu Val Thr Val Ser Ser Ala
        115                 120                 125
```

<210> SEQ ID NO 12
<211> LENGTH: 333
<212> TYPE: DNA
<213> ORGANISM: Artificial sequence
<220> FEATURE:
<221> NAME/KEY: CDS
<222> LOCATION: (1)..(333)
<223> OTHER INFORMATION: Synthetic construct -
      variable region of the light chain for artificial IgG

<400> SEQUENCE: 12

```
gat att gta ttg acc cag tct cca gcc acc ctg tct ttg tct cca ggg           48
Asp Ile Val Leu Thr Gln Ser Pro Ala Thr Leu Ser Leu Ser Pro Gly
1               5                   10                  15 gaa aga gcc acc ctc tcc tgc agg gcc agt cag agt gtt agc agc tac           96
Glu Arg Ala Thr Leu Ser Cys Arg Ala Ser Gln Ser Val Ser Ser Tyr
            20                  25                  30 tta gcc tgg ttc caa cag aaa cct ggc cag gct ccc agg ctc ctc atc          144
Leu Ala Trp Phe Gln Gln Lys Pro Gly Gln Ala Pro Arg Leu Leu Ile
        35                  40                  45 tat gat gca tcc aac agg gcc act ggc gtc cca gcc agg ttc agt ggc          192
Tyr Asp Ala Ser Asn Arg Ala Thr Gly Val Pro Ala Arg Phe Ser Gly
    50                  55                  60
```

```
agt ggg tct ggg aca gac ttc act ctc acc atc acc agc cta gag cct    240
Ser Gly Ser Gly Thr Asp Phe Thr Leu Thr Ile Thr Ser Leu Glu Pro
 65                  70                  75                  80 gaa gat ttt gca gtt tat tac tgt cag cag cgt ggc gac tgg ccg ctc    288
Glu Asp Phe Ala Val Tyr Tyr Cys Gln Gln Arg Gly Asp Trp Pro Leu
                 85                  90                  95 act ttc ggc gga ggg acc aag gtg gaa atc aaa cga act gtg gcg        333
Thr Phe Gly Gly Gly Thr Lys Val Glu Ile Lys Arg Thr Val Ala
            100                 105                 110

<210> SEQ ID NO 13
<211> LENGTH: 369
<212> TYPE: DNA
<213> ORGANISM: Artificial sequence
<220> FEATURE:
<221> NAME/KEY: CDS
<222> LOCATION: (1)..(369)
<223> OTHER INFORMATION: Synthetic construct -
      variable region of the heavy chain for artificial IgG

<400> SEQUENCE: 13 cag gtg cag ctg gtg caa tct ggc cca gga ctg gtg aag cct tcg gag     48
Gln Val Gln Leu Val Gln Ser Gly Pro Gly Leu Val Lys Pro Ser Glu
1               5                   10                  15 acc ctg tcc ctc acc tgc act gtc tct ggt ggc tcc gtc agc agt ggt     96
Thr Leu Ser Leu Thr Cys Thr Val Ser Gly Gly Ser Val Ser Ser Gly
            20                  25                  30 act tac tgc tgg agc tgg atc cgg cag ccc cca ggg aag gga ctg gag    144
Thr Tyr Cys Trp Ser Trp Ile Arg Gln Pro Pro Gly Lys Gly Leu Glu
        35                  40                  45 tgg att gcg tat atc tgt aac agt ggg agc acc agc tac aac ccc tcc    192
Trp Ile Ala Tyr Ile Cys Asn Ser Gly Ser Thr Ser Tyr Asn Pro Ser
    50                  55                  60 ctc aag agt cga ggc acc ata tca gta gac acg tcc aag aac cag ttc    240
Leu Lys Ser Arg Gly Thr Ile Ser Val Asp Thr Ser Lys Asn Gln Phe
 65                 70                  75                  80 tcc cta agg ctg agc tct gtg acc gct gcg gac acg gcc gta tat tac    288
Ser Leu Arg Leu Ser Ser Val Thr Ala Ala Asp Thr Ala Val Tyr Tyr
                 85                 90                  95 tgt gcg aga ttg tcg cta ata atg gtg tat cat atc ttt gac tac tgg    336
Cys Ala Arg Leu Ser Leu Ile Met Val Tyr His Ile Phe Asp Tyr Trp
            100                 105                 110 ggg cag gga acc ctg gtc acc gtc tcc tca gcg                        369
Gly Gln Gly Thr Leu Val Thr Val Ser Ser Ala
            115                 120

<210> SEQ ID NO 14
<211> LENGTH: 351
<212> TYPE: DNA
<213> ORGANISM: Artificial sequence
<220> FEATURE:
<221> NAME/KEY: CDS
<222> LOCATION: (1)..(351)
<223> OTHER INFORMATION: Synthetic construct -
      variable region of the light chain for artificial IgG

<400> SEQUENCE: 14 gat att gtg atg acg cag act cca gac tcc ctg gct gtg tct ctg ggc     48
Asp Ile Val Met Thr Gln Thr Pro Asp Ser Leu Ala Val Ser Leu Gly
1               5                   10                  15 gag agg gcc acc atc aac tgc aag tcc agt cag aat ctc tta tac act     96
Glu Arg Ala Thr Ile Asn Cys Lys Ser Ser Gln Asn Leu Leu Tyr Thr
            20                  25                  30 tcc agt aat cag acc tac tta gct tgg tac cag cag aaa cca gga cag    144
```

```
                Ser Ser Asn Gln Thr Tyr Leu Ala Trp Tyr Gln Gln Lys Pro Gly Gln
                        35                  40                  45 cct cct aaa ttg ctc att tac tgg gca tct acg cgg gag tcc ggg gtc          192
Pro Pro Lys Leu Leu Ile Tyr Trp Ala Ser Thr Arg Glu Ser Gly Val
        50                  55                  60 cct gac cga ttc agt ggc agc ggg tct ggg aca gat ttc act ctg acc          240
Pro Asp Arg Phe Ser Gly Ser Gly Ser Gly Thr Asp Phe Thr Leu Thr
65                  70                  75                  80 atc agc agc ctg cag cct gaa gat gtg gca gca tat tac tgt cag caa          288
Ile Ser Ser Leu Gln Pro Glu Asp Val Ala Ala Tyr Tyr Cys Gln Gln
                85                  90                  95 tat tat agg act cct atc act ttc ggc cct ggg acc aag gtg gag atc          336
Tyr Tyr Arg Thr Pro Ile Thr Phe Gly Pro Gly Thr Lys Val Glu Ile
                100                 105                 110 aaa cga act gtg gcg                                                      351
Lys Arg Thr Val Ala
                115

<210> SEQ ID NO 15
<211> LENGTH: 375
<212> TYPE: DNA
<213> ORGANISM: Artificial sequence
<220> FEATURE:
<221> NAME/KEY: CDS
<222> LOCATION: (1)..(375)
<223> OTHER INFORMATION: Synthetic construct -
      variable region of the heavy chain for artificial IgG

<400> SEQUENCE: 15 cag gtg cag ctg gtg gag tct ggg gct gag gtg agg aag cct ggg gcc          48
Gln Val Gln Leu Val Glu Ser Gly Ala Glu Val Arg Lys Pro Gly Ala
1               5                   10                  15 tca gtg aag gtc tcc tgt cag gcc tct gga tac acc ttc acc gac cac          96
Ser Val Lys Val Ser Cys Gln Ala Ser Gly Tyr Thr Phe Thr Asp His
                20                  25                  30 tat ctc cac tgg ctg cga cag gcc ccc gga caa ggg ctt gag tgg atg          144
Tyr Leu His Trp Leu Arg Gln Ala Pro Gly Gln Gly Leu Glu Trp Met
            35                  40                  45 ggg tgg atc aat ccc aac atc att gaa gcc aga tac gtc gca cgg aag          192
Gly Trp Ile Asn Pro Asn Ile Ile Glu Ala Arg Tyr Val Ala Arg Lys
        50                  55                  60 ttt aga ggc agt gtc aac ctg acc agg gac acg gcc atc cag aca gtg          240
Phe Arg Gly Ser Val Asn Leu Thr Arg Asp Thr Ala Ile Gln Thr Val
65                  70                  75                  80 tac ata gaa atg agc cgc ctg aca tct gac gac acg gcc acc tac ttc          288
Tyr Ile Glu Met Ser Arg Leu Thr Ser Asp Asp Thr Ala Thr Tyr Phe
                85                  90                  95 tgt gcg aga gcg tta aag gag ggc gga tat agt tat ggt tat tac gac          336
Cys Ala Arg Ala Leu Lys Glu Gly Gly Tyr Ser Tyr Gly Tyr Tyr Asp
                100                 105                 110 cat tgg ggc ccg gga acc ctg gtc act gtc tcc tca gcg                      375
His Trp Gly Pro Gly Thr Leu Val Thr Val Ser Ser Ala
            115                 120                 125

<210> SEQ ID NO 16
<211> LENGTH: 345
<212> TYPE: DNA
<213> ORGANISM: Artificial sequence
<220> FEATURE:
<221> NAME/KEY: CDS
<222> LOCATION: (1)..(345)
<223> OTHER INFORMATION: Synthetic construct -
      variable region of the light chain for artificial IgG
```

```
<400> SEQUENCE: 16 gaa att gtg atg act cag tct ccc tgc ccg tca ccc ctg gag agc cgg        48
Glu Ile Val Met Thr Gln Ser Pro Cys Pro Ser Pro Leu Glu Ser Arg
1               5                   10                  15 cct cca tct cct gca ggt cta gtc aga gcc tct tgg ata gcg atg atg        96
Pro Pro Ser Pro Ala Gly Leu Val Arg Ala Ser Trp Ile Ala Met Met
            20                  25                  30 gcg aca cct att tgg act ggt acc tgc aga agc cag ggc agt ctc cac       144
Ala Thr Pro Ile Trp Thr Gly Thr Cys Arg Ser Gln Gly Ser Leu His
        35                  40                  45 agc tcc tcg atc tat acc ctt tcc cat cgg gcc cct gga gtc cca gac       192
Ser Ser Ser Ile Tyr Thr Leu Ser His Arg Ala Pro Gly Val Pro Asp
    50                  55                  60 agg ttc agt ggc agt ggg tca ggc act gat ttc aca ctg aaa atc agc       240
Arg Phe Ser Gly Ser Gly Ser Gly Thr Asp Phe Thr Leu Lys Ile Ser
65                  70                  75                  80 agg gtg gag gct gag gat gtt gga gtt tat tac tgc ctg caa cgt ata       288
Arg Val Glu Ala Glu Asp Val Gly Val Tyr Tyr Cys Leu Gln Arg Ile
                85                  90                  95 gac ttt cca ttc act ttc ggc cca ggg acc aag gtg gaa atc aaa cga       336
Asp Phe Pro Phe Thr Phe Gly Pro Gly Thr Lys Val Glu Ile Lys Arg
                100                 105                 110 act gtg gcg                                                            345
Thr Val Ala
        115

<210> SEQ ID NO 17
<211> LENGTH: 6188
<212> TYPE: DNA
<213> ORGANISM: Artificial sequence
<220> FEATURE:
<223> OTHER INFORMATION: Synthetic construct - plasmid DNA

<400> SEQUENCE: 17
ggatctgcga tcgctccggt gcccgtcagt gggcagagcg cacatcgccc acagtccccg        60
agaagttggg gggaggggtc ggcaattgaa cgggtgccta gagaaggtgg cgcggggtaa       120
actgggaaag tgatgtcgtg tactggctcc gcctttttcc cgagggtggg ggagaaccgt       180
atataagtgc agtagtcgcc gtgaacgttc tttttcgcaa cgggtttgcc gccagaacac       240
agctgaagct cgaggggctc gcatctctc cttcacgcgc ccgccgccct acctgaggcc       300
gccatccacg ccggttgagt cgcgttctgc cgcctcccgc ctgtggtgcc tcctgaactg       360
cgtccgccgt ctaggtaagt ttaaagctca ggtcgagacc gggcctttgt ccggcgctcc       420
cttggagcct acctagactc agccggctct ccacgctttg cctgaccctg cttgctcaac       480
tctacgtctt tgtttcgttt ctgttctgc gccgttacag atccaagctg tgaccggcgc       540
ctacctgaga tcaccggcgc accatggat atcctgtgca gcaccctgct cctgctcacc       600
gtgccttccg tgctgtctag agacggatcc aatagaccag ttgcaatcca acgagagtc       660 taatagaatg aggtcgaaaa gtaaatcgcg cgggtttgtt actgataaag caggcaagac       720
ctaaaatgtg taagggcaa agtgtatact ttggcgtcac cccttacata ttttaggtct       780 tttttttattg tgcgtaacta acttgccatc ttcaaacagg agggctggaa gaagcagacc       840
gctaacacag tacataaaaa aggagacatg aacgatgaac atcaaaaagt ttgcaaaaca       900
agcaacagta ttaaccttta ctaccgcact gctggcagga ggcgcaactc aagcgtttgc       960
gaaagaaacg aaccaaaagc catataagga aacatacgcc atttcccata ttacacgcca      1020
tgatatgctg caaatccctg aacagcaaaa aaatgaaaaa tatcaagttc ctgagttcga      1080
```

```
ttcgtccaca attaaaaata tctcttctgc aaaaggcctg gacgtttggg acagctggcc    1140
attacaaaac gctgacggca ctgtcgcaaa ctatcacggc taccacatcg tctttgcatt    1200
agccggagat cctaaaaatg cggatgacac atcgatttac atgttctatc aaaaagtcgg    1260
cgaaacttct attgacagct ggaaaaacgc tggccgcgtc tttaaagaca gcgacaaatt    1320
cgatgcaaat gattctatcc taaaagacca aacacaagaa tggtcaggtt cagccacatt    1380
tacatctgac ggaaaaatcc gtttattcta cactgatttc tccggtaaac attacggcaa    1440
acaaacactg acaactgcac aagttaacgt atcagcatca gacagctctt tgaacatcaa    1500
cggtgtagag gattataaat caatctttga cggtgacgga aaaacgtatc aaaatgtaca    1560
gcagttcatc gatgaaggca actacagctc aggcgacaac catacgctga gagatcctca    1620
ctacgtagaa gataaaggcc acaaatactt agtatttgaa gcaaacactg gaactgaaga    1680
tggctaccaa ggcgaagaat ctttatttaa caaagcatac tatggcaaaa gcacatcatt    1740
cttccgtcaa gaaagtcaaa aacttctgca aagcgataaa aaacgcacgg ctgagttagc    1800
aaacggcgct ctcggtatga ttgagctaaa cgatgattac acactgaaaa agtgatgaa    1860 accgctgatt gcatctaaca cagtaacaga tgaaattgaa cgcgcgaacg tctttaaaat    1920
gaacggcaaa tggtacctgt tcactgactc ccgcggatca aaaatgacga ttgacggcat    1980
tacgtctaac gatatttaca tgcttggtta tgtttctaat tctttaactg cccatacaa    2040 gccgctgaac aaaactggcc ttgtgttaaa aatggatctt gatcctaacg atgtaacctt    2100
tacttactca cacttcgctg tacctcaagc gaaaggaaac aatgtcgtga ttacaagcta    2160
tatgacaaac agaggattct acgcagacaa acaatcaacg tttgcgccta gcttcctgct    2220
gaacatcaaa ggcaagaaaa catctgttgt caaagacagc atccttgaac aaggacaatt    2280
aacagttaac aaataaaaac gcaaagaaaa atgcagatat cctattggca ttgacgtctc    2340
gtcgaccaag ggcccatcgg tcttcccccct ggcaccctcc tccaagagca cctctggggg    2400
cacagcggcc ctgggctgcc tggtcaagga ctacttcccc gaaccggtga cggtgtcgtg    2460
gaactcaggc gccctgacca gcggcgtgca caccttcccg gctgtcctac agtcctcagg    2520
actctactcc ctcagcagcg tggtgaccgt gccctccagc agcttgggca cccagaccta    2580
catctgcaac gtgaatcaca agcccagcaa caccaaggtg gacaagagag ttgagcccaa    2640
atcttgtgac aaaactcaca catgcccacc gtgcccagca cctgaactcc tggggggacc    2700
gtcagtcttc ctcttccccc caaaacccaa ggacaccctc atgatctccc ggaccctga    2760 ggtcacatgc gtggtggtgg acgtgagcca cgaagaccct gaggtcaagt tcaactggta    2820
cgtggacggc gtggaggtgc ataatgccaa gacaaagccg cgggaggagc agtacaacag    2880
cacgtaccgt gtggtcagcg tcctcaccgt cctgcaccag gactggctga atggcaagga    2940
gtacaagtgc aaggtctcca acaaagccct cccagccccc atcgagaaaa ccatctccaa    3000
agccaaaggg cagccccgag aaccacaggt gtacaccctg cccccatccc gggaggagat    3060
gaccaagaac caggtcagcc tgacctgcct ggtcaaaggc ttctatccca gcgacatcgc    3120
cgtggagtgg gagagcaatg ggcagccgga gaacaactac aagaccacgc ctcccgtgct    3180
ggactccgac ggctccttct cctctacag caagctcacc gtggacaaga gcaggtggca    3240 gcagggaac gtcttctcat gctccgtgat gcacgaggct ctgcacaacc actacacgca    3300
gaagagcctc tccctgtctc cgggtaaatg agtgctagct ggccagacat gataagatac    3360
attgatgagt ttggacaaac cacaactaga atgcagtgaa aaaaatgctt tatttgtgaa    3420
```

```
atttgtgatg ctattgcttt atttgtaacc attataagct gcaataaaca agttaacaac    3480
aacaattgca ttcattttat gtttcaggtt caggggagg tgtgggaggt ttttaaagc      3540 aagtaaaacc tctacaaatg tggtatggaa ttaattctaa aatacagcat agcaaaactt    3600
taacctccaa atcaagcctc tacttgaatc cttttctgag ggatgaataa ggcataggca    3660 tcagggctg ttgccaatgt gcattagctg tttgcagcct caccttcttt catggagttt     3720
aagatatagt gtattttccc aaggtttgaa ctagctcttc atttctttat gttttaaatg    3780
cactgacctc ccacattccc tttttagtaa aatattcaga aataatttaa atacatcatt    3840
gcaatgaaaa taaatgtttt ttattaggca gaatccagat gctcaaggcc cttcataata    3900 tccccagtt tagtagttgg acttagggaa caaaggaacc tttaatagaa attggacagc     3960
aagaaagcga gcttctagct tatcctcagt cctgctcctc tgccacaaag tgcacgcagt    4020
tgccggccgg gtcgcgcagg gcgaactccc gcccccacgg ctgctcgccg atctcggtca    4080
tggccggccc ggaggcgtcc cggaagttcg tggacacgac ctccgaccac tcggcgtaca    4140
gctcgtccag gccgcgcacc cacacccagg ccagggtgtt gtccggcacc acctggtcct    4200
ggaccgcgct gatgaacagg gtcacgtcgt cccggaccac cccggcgaag tcgtcctcca    4260
cgaagtcccg ggagaacccg agccggtcgg tccagaactc gaccgctccg gcgacgtcgc    4320
gcgcggtgag caccggaacg gcactggtca acttggccat gatggctcct cctgtcagga    4380
gaggaaagag aagaaggtta gtacaattgc tatagtgagt tgtattatac tatgcagata    4440
tactatgcca atgattaatt gtcaaactag ggctgcaggg ttcatagtgc cacttttcct    4500
gcactgcccc atctcctgcc cacccttcc caggcataga cagtcagtga cttaccaaac    4560
tcacaggagg gagaaggcag aagcttgaga cagacccgcg ggaccgccga actgcgaggg    4620
gacgtggcta gggcggcttc tttatggtg cgccggccct cggaggcagg gcgctcgggg     4680
aggcctagcg gccaatctgc ggtggcagga ggcggggccg aaggccgtgc ctgaccaatc    4740
cggagcacat aggagtctca gcccccgcc ccaaagcaag gggaagtcac gcgcctgtag     4800
cgccagcgtg ttgtgaaatg ggggcttggg ggggttgggg ccctgactag tcaaaacaaa    4860
ctcccattga cgtcaatggg gtggagactt ggaaatcccc gtgagtcaaa ccgctatcca    4920
cgcccattga tgtactgcca aaaccgcatc atcatggtaa tagcgatgac taatacgtag    4980
atgtactgcc aagtaggaaa gtcccataag gtcatgtact gggcataatg ccaggcgggc    5040
catttaccgt cattgacgtc aataggggc gtacttggca tatgatacac ttgatgtact     5100
gccaagtggg cagtttaccg taaatactcc acccattgac gtcaatggaa agtccctatt    5160
ggcgttacta tgggaacata cgtcattatt gacgtcaatg ggcggggtc gttgggcggt     5220 cagccaggcg ggccatttac cgtaagttat gtaacgcctg caggttaatt aagaacatgt    5280
gagcaaaagg ccagcaaaag gccaggaacc gtaaaaaggc cgcgttgctg gcgttttcc     5340 ataggctccg ccccctgac gagcatcaca aaaatcgacg ctcaagtcag aggtggcgaa     5400
acccgacagg actataaaga taccaggcgt ttccccctgg aagctccctc gtgcgctctc    5460
ctgttccgac cctgccgctt accggatacc tgtccgcctt tctcccttcg ggaagcgtgg    5520
cgctttctca tagctcacgc tgtaggtatc tcagttcggt gtaggtcgtt cgctccaagc    5580
tgggctgtgt gcacgaaccc cccgttcagc ccgaccgctg cgccttatcc ggtaactatc    5640
gtcttgagtc caacccggta agacacgact tatcgccact ggcagcagcc actggtaaca    5700
ggattagcag agcgaggtat gtaggcggtg ctacagagtt cttgaagtgg tggcctaact    5760
acggctacac tagaagaaca gtatttggta tctgcgctct gctgaagcca gttaccttcg    5820
```

```
gaaaaagagt tggtagctct tgatccggca acaaaccac cgctggtagc ggtggttttt    5880
ttgtttgcaa gcagcagatt acgcgcagaa aaaaggatc tcaagaagat cctttgatct    5940
tttctacggg gtctgacgct cagtggaacg aaaactcacg ttaagggatt ttggtcatgg    6000
ctagttaatt aacatttaaa tcagcggccg caataaaata tctttatttt cattacatct    6060
gtgtgttggt tttttgtgtg aatcgtaact aacatacgct ctccatcaaa acaaaacgaa    6120
acaaaacaaa ctagcaaaat aggctgtccc cagtgcaagt gcaggtgcca gaacatttct    6180
ctatcgaa                                                            6188
```

<210> SEQ ID NO 18
<211> LENGTH: 5946
<212> TYPE: DNA
<213> ORGANISM: Artificial sequence
<220> FEATURE:
<223> OTHER INFORMATION: Synthetic construct - plasmid DNA

<400> SEQUENCE: 18

```
ggatctgcga tcgctccggt gcccgtcagt gggcagagcg cacatcgccc acagtccccg      60
agaagttggg gggagggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc tttttcgcaa cgggtttgcc gccagaacac     240
agctgaagct cgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctgactc agccggtctc ccacgctttg cctgaccctg cttgctcaac     480
tctacgtctt tgtttcgttt tctgttctgc gccgttacag atccaagctg tgaccggcgc     540
ctacctgaga tcaccggcgc caccatgcgc ctgctcgccc agctgctcgg cctgctcatg     600
ctgtgggtgc ctagctccgg cgagacggat ccaatagacc agttgcaatc caaacgagag     660
tctaatagaa tgaggtcgaa agtaaatcg cgcgggtttg ttactgataa agcaggcaag     720
acctaaaatg tgtaaagggc aaagtgtata ctttggcgtc accccttaca tattttaggt     780
ctttttttat tgtgcgtaac taacttgcca tcttcaaaca ggagggctgg aagaagcaga     840
ccgctaacac agtacataaa aaggagaca tgaacgatga acatcaaaaa gtttgcaaaa     900
caagcaacag tattaacctt tactaccgca ctgctggcag gaggcgcaac tcaagcgttt     960 gcgaagaaa cgaaccaaaa gccatataag gaaacatacg gcatttccca tattacacgc    1020
catgatatgc tgcaaatccc tgaacagcaa aaaatgaaa atatcaagt tcctgagttc    1080 gattcgtcca caattaaaaa tatctcttct gcaaaggcc tggacgtttg gacagctgg    1140 ccattacaaa acgctgacgg cactgtcgca actatcacg gctaccacat cgtctttgca    1200
ttagccggag atcctaaaaa tgcggatgac acatcgattt acatgttcta tcaaaaagtc    1260
ggcgaaactt ctattgacag ctggaaaaac gctggccgcg tctttaaaga cagcgacaaa    1320
ttcgatgcaa atgattctat cctaaaagac caaacacaag aatggtcagg ttcagccaca    1380
tttacatctg acgaaaaat ccgtttattc tacactgatt tctccggtaa acattacggc    1440
aaacaaacac tgacaactgc acaagttaac gtatcagcat cagacagctc tttgaacatc    1500
aacggtgtag aggattataa atcaatcttt gacggtgacg gaaaaacgta tcaaaatgta    1560
cagcagttca tcgatgaagg caactacagc tcaggcgaca ccatacgct gagagatcct    1620
```

-continued

```
cactacgtag aagataaagg ccacaaatac ttagtatttg aagcaaacac tggaactgaa    1680
gatggctacc aaggcgaaga atctttattt aacaaagcat actatggcaa aagcacatca    1740
ttcttccgtc aagaaagtca aaaacttctg caaagcgata aaaacgcac ggctgagtta     1800
gcaaacggcg ctctcggtat gattgagcta acgatgatt acacactgaa aaagtgatg      1860
aaaccgctga ttgcatctaa cacagtaaca gatgaaattg aacgcgcgaa cgtcttttaaa   1920
atgaacggca aatggtacct gttcactgac tcccgcggat caaaaatgac gattgacggc   1980
attacgtcta acgatattta catgcttggt tatgtttcta attctttaac tggcccatac   2040
aagccgctga acaaaactgg ccttgtgtta aaaatggatc ttgatcctaa cgatgtaacc    2100
tttacttact cacacttcgc tgtacctcaa gcgaaggaa acaatgtcgt gattacaagc    2160
tatatgacaa acagaggatt ctacgcagac aaacaatcaa cgtttgcgcc tagcttcctg   2220
ctgaacatca aaggcaagaa acatctgtt gtcaaagaca gcatccttga acaaggacaa    2280
ttaacagtta acaataaga tatcctattg gcattgacgt ctcgataaga tatcctattg    2340
gcattgacgt ctcggcccca tctgtcttca tcttcccgcc atctgatgag cagttgaaat   2400
ctggaactgc ctctgttgtg tgcctgctga ataacttcta tcccagagag gccaaagtac   2460
agtggaaggt ggataacgcc ctccaatcgg gtaactccca ggagagtgtc acagagcagg   2520
acagcaagga cagcacctac agcctcagca gcaccctgac gctgagcaaa gcagactacg   2580
agaaacacaa agtctacgcc tgcgaagtca cccatcaggg cctgagctcg cccgtcacaa   2640
agagcttcaa caggggagag tgttgataag ctagctggcc agacatgata agatacattg    2700
atgagtttgg acaaaccaca actagaatgc agtgaaaaaa atgctttatt tgtgaaattt    2760
gtgatgctat tgcttatttt gtaaccatta taagctgcaa taaacaagtt aacaacaaca    2820
attgcattca ttttatgttt caggttcagg gggaggtgtg ggaggttttt taaagcaagt    2880
aaaacctcta caaatgtggt atggaattaa ttctaaaata cagcatagca aaactttaac    2940
ctccaaatca agcctctact tgaatccttt tctgagggat gaataaggca taggcatcag    3000
gggctgttgc caatgtgcat tagctgtttg cagcctcacc ttctttcatg gagtttaaga    3060
tatagtgtat tttcccaagg tttgaactag ctcttcattt ctttatgttt taaatgcact    3120
gacctcccac attcccttt tagtaaaata ttcagaaata atttaaatac atcattgcaa     3180
tgaaaataaa tgttttttat taggcagaat ccagatgctc aaggcccttc ataatatccc    3240
ccagtttagt agttggactt agggaacaaa ggaacctta atagaaattg gacagcaaga     3300
aagcgagctt ctagcttatc ttatcagaag aactcgtcaa gaaggcgata gaaggcgatg   3360
cgctgcgaat cgggagcggc gataccgtaa agcacgagga agcggtcagc ccattcgccg   3420
ccaagctctt cagcaatatc acgggtagcc aacgctatgt cctgatagcg gtccgccaca   3480
cccagccggc cacagtcgat gaatccagaa aagcggccat tttccaccat gatattcggc   3540
aagcaggcat cgccatgggt cacgacgaga tcctcgccgt cgggcatgct cgccttgagc   3600
ctggcgaaca gttcggctgg cgcgagcccc tgatgctctt cgtccagatc atcctgatcg   3660
acaagaccgg cttccatccg agtacgtgct cgctcgatgc gatgtttcgc ttcctcctcg   3720
aatgggcagg tagccggatc aagcgtatgc agccgccgca ttgcatcagc catgatggat   3780
actttctcgg caggagcaag gtgagatgac aggagatcct gccccggcac ttcgcccaat   3840
agcagccagt cccttcccgc ttcagtgaca acgtcgagca cagctgcgca aggaacgccc   3900
gtcgtggcca gccacgatag ccgcgctgcc tcgtcttgca gttcattcag ggcaccggac   3960
aggtcggtct tgacaaaaag aaccgggcgc ccctgcgctg acagccggaa cacggcggca   4020
```

```
tcagagcagc cgattgtctg ttgtgcccag tcatagccga atagcctctc cacccaagcg   4080
gccggagaac ctgcgtgcaa tccatcttgt tcaatcatga tggctcctcc tgtcaggaga   4140
ggaaagagaa gaaggttagt acaattgcta tagtgagttg tattatacta tgcagatata   4200
ctatgccaat gattaattgt caaactaggg ctgcagggtt catagtgcca cttttcctgc   4260
actgccccat ctcctgccca ccctttccca ggcatagaca gtcagtgact taccaaactc   4320
acaggaggga gaaggcagaa gcttgagaca gacccgcggg accgccgaac tgcgagggga   4380
cgtggctagg gcggcttctt ttatggtgcg ccggccctcg gaggcagggc gctcggggag   4440
gcctagcggc caatctgcgg tggcaggagg cggggccgaa ggccgtgcct gaccaatccg   4500
gagcacatag gagtctcagc ccccgcccc aaagcaaggg gaagtcacgc gcctgtagcg   4560
ccagcgtgtt gtgaaatggg ggcttggggg ggttggggcc ctgactagtc aaaacaaact   4620
cccattgacg tcaatggggt ggagacttgg aaatccccgt gagtcaaacc gctatccacg   4680
cccattgatg tactgccaaa accgcatcat catggtaata gcgatgacta atacgtagat   4740
gtactgccaa gtaggaaagt cccataaggt catgtactgg gcataatgcc aggcgggcca   4800
tttaccgtca ttgacgtcaa tagggggcgt acttggcata tgatacactt gatgtactgc   4860
caagtgggca gtttaccgta atactccacc cattgacgt caatggaaag tccctattgg   4920
cgttactatg ggaacatacg tcattattga cgtcaatggg cggggtcgt tgggcggtca   4980 gccaggcggg ccatttaccg taagttatgt aacgcctgca ggttaattaa gaacatgtga   5040
gcaaaaggcc agcaaaaggc caggaaccgt aaaaaggccg cgttgctggc gtttttccat   5100
aggctccgcc ccctgacga gcatcacaaa aatcgacgct caagtcagag gtggcgaaac   5160
ccgacaggac tataaagata ccaggcgttt ccccctggaa gctccctcgt gcgctctcct   5220
gttccgaccc tgccgcttac cggatacctg tccgcctttc tcccttcggg aagcgtggcg   5280
ctttctcata gctcacgctg taggtatctc agttcggtgt aggtcgttcg ctccaagctg   5340
ggctgtgtgc acgaaccccc cgttcagccc gaccgctgcg ccttatccgg taactatcgt   5400
cttgagtcca acccggtaag acacgactta tcgccactgg cagcagccac tggtaacagg   5460
attagcagag cgaggtatgt aggcggtgct acagagttct tgaagtggtg gcctaactac   5520
ggctacacta agaacagt atttggtatc tgcgctctgc tgaagccagt taccttcgga   5580
aaaagagttg gtagctcttg atccggcaaa caaaccaccg ctggtagcgg tggtttttttt   5640 gtttgcaagc agcagattac gcgcagaaaa aaggatctc aagaagatcc tttgatcttt   5700
tctacggggt ctgacgctca gtggaacgaa aactcacgtt aagggatttt ggtcatggct   5760
agttaattaa catttaaatc agcggccgca ataaatatc tttatttca ttacatctgt   5820 gtgttggttt tttgtgtgaa tcgtaactaa catacgctct ccatcaaaac aaaacgaaac   5880
aaaacaaact agcaaaatag gctgtcccca gtgcaagtgc aggtgccaga acatttctct   5940
atcgaa                                                              5946
```

<210> SEQ ID NO 19
<211> LENGTH: 23
<212> TYPE: DNA
<213> ORGANISM: Artificial sequence
<220> FEATURE:
<223> OTHER INFORMATION: Synthetic construct - primer

<400> SEQUENCE: 19
gtgtccttgg gttttggggg gaa                                             23

```
<210> SEQ ID NO 20
<211> LENGTH: 23
<212> TYPE: DNA
<213> ORGANISM: Artificial sequence
<220> FEATURE:
<223> OTHER INFORMATION: Synthetic construct - primer

<400> SEQUENCE: 20
gtagtccttg accaggcagc cct                                              23

<210> SEQ ID NO 21
<211> LENGTH: 24
<212> TYPE: DNA
<213> ORGANISM: Artificial Sequence
<220> FEATURE:
<223> OTHER INFORMATION: Synthetic construct - primer

<400> SEQUENCE: 21
caccggcgcc accatgcgcc tgct                                             24

<210> SEQ ID NO 22
<211> LENGTH: 29
<212> TYPE: DNA
<213> ORGANISM: Artificial sequence
<220> FEATURE:
<223> OTHER INFORMATION: Synthetic construct - primer

<400> SEQUENCE: 22
ggcctctctg ggatagaagt tattcagca                                        29
```